(12) United States Patent
Canfield et al.

(10) Patent No.: US 12,253,460 B2
(45) Date of Patent: Mar. 18, 2025

(54) DRUG DETECTION USING COBALT THIOCYANATE AND EOSIN Y

(71) Applicants: Bowling Green State University, Bowling Green, OH (US); Vuronyx Technologies LLC, Woburn, MA (US)

(72) Inventors: Jeremy Canfield, Bowling Green, OH (US); Jon Sprague, Bowling Green, OH (US); Sandip Agarwal, Woburn, MA (US); Kateland Herault, Woburn, MA (US); Mark Benjamin Volkin, Walpole, MA (US)

(73) Assignees: Bowling Green State University, Bowling Green, OH (US); Vuronyx Technologies LLC, Woburn, MA (US)

( * ) Notice: Subject to any disclaimer, the term of this patent is extended or adjusted under 35 U.S.C. 154(b) by 243 days.

(21) Appl. No.: 17/910,926

(22) PCT Filed: Mar. 11, 2021

(86) PCT No.: PCT/US2021/021824
§ 371 (c)(1),
(2) Date: Sep. 12, 2022

(87) PCT Pub. No.: WO2021/183719
PCT Pub. Date: Sep. 16, 2021

(65) Prior Publication Data
US 2023/0137342 A1    May 4, 2023

Related U.S. Application Data

(60) Provisional application No. 63/049,805, filed on Jul. 9, 2020, provisional application No. 62/988,676, filed on Mar. 12, 2020.

(51) Int. Cl.
*B01L 3/00*    (2006.01)
*B01F 33/302*    (2022.01)
(Continued)

(52) U.S. Cl.
CPC .................................. *G01N 21/29* (2013.01)

(58) Field of Classification Search
CPC .. G01N 21/29; G01N 33/9486; G01N 33/523; C40B 60/12
See application file for complete search history.

(56) References Cited

U.S. PATENT DOCUMENTS

2004/0137551 A1* 7/2004 Markovic ................ C12Q 1/42
                                                              435/21
2010/0197516 A1* 8/2010 Holmes .................. G01N 31/22
                                                              506/9
2018/0340298 A1* 11/2018 Bollstrom .............. D21H 21/48

FOREIGN PATENT DOCUMENTS

WO    WO-2009148885 A2 * 12/2009 ............... G01N 1/30
WO    WO-2019095073 A1 *  5/2019 ......... A61K 41/0057

OTHER PUBLICATIONS

Jiang, Gang-Biao, et al. "Potential biosorbent based on sugarcane bagasse modified with tetraethylenepentamine for removal of eosin Y." International journal of biological macromolecules 50.3 (2012): 707-712. (Year: 2012).*

(Continued)

*Primary Examiner* — Travis M Figg
*Assistant Examiner* — Oyeleye Alexander Alabi
(74) *Attorney, Agent, or Firm* — MacMillan, Sobanski & Todd, LLC

(57) ABSTRACT

Materials and methods for testing unknown substances for the presence of an opioid are described.

14 Claims, 28 Drawing Sheets
(26 of 28 Drawing Sheet(s) Filed in Color)

(51) Int. Cl.
*B01F 33/3033* (2022.01)
*B01L 7/00* (2006.01)
*C12Q 1/6848* (2018.01)
*C12Q 1/686* (2018.01)
*G01N 21/29* (2006.01)

(56) References Cited

OTHER PUBLICATIONS

Biognost "Eosin Y powder dye, C.I. 45380" (Year: 2015).*
Kangas et al., "A New Possible Alternative Colorimetric Drug Detection Test for Fentanyl", Organic and Medicinal Chemistry International Journal, 2017, vol. 4, pp. 001-003.
International Search Report and Written Opinion, Application No. PCT/US21/21824, dated Jul. 21, 2021.

* cited by examiner control                    heroin control                    heroin

DRUG DETECTION USING COBALT THIOCYANATE AND EOSIN Y

RELATED APPLICATIONS

This is the national phase entry of international application PCT/US2021/21824, filed under the authority of the Patent Cooperation Treaty on Mar. 11, 2021, published; which claims priority to U.S. Provisional Application No. 62/988,676 filed under 35 U.S.C. § 111(b) on Mar. 12, 2020, and U.S. Provisional Application No. 63/049,805 filed under 35 U.S.C. § 111(b) on Jul. 9, 2020. The entire disclosure of each the aforementioned applications is incorporated herein by reference for all purposes.

STATEMENT REGARDING FEDERALLY SPONSORED RESEARCH

This invention was made with no government support. The government has no rights in this invention.

BACKGROUND

Opioid abuse has increased dramatically in the last decade, leading to increased overdoses and deaths. The opioid epidemic continues to harm communities across the United States, causing growing numbers of overdoses and accidental exposure to various drugs. One of the most dangerous drugs is fentanyl, a synthetic opioid, and its various structural analogs that are appearing increasingly frequently on the street.

Fentanyl is a synthetic opioid that pharmacologically functions as an agonist at the μ opioid receptor. Currently being manufactured around the world illicitly, mainly in China, the number of fentanyl drug seizures has increased significantly. In 2018, the National Forensic Laboratory Information System (NFLIS) report indicated an almost 50,000 case increase from 2016. In 2016, the amount of fentanyl cases reported nationally was 34,204, with 83,765 cases being reported in 2018. In addition to being used therapeutically as a pain medication, fentanyl is also being added as an adulterant to other street drugs such as heroin and other opioids. With a lethal dose of just two milligrams, fentanyl is typically found in mixtures of other drugs including heroin and other opiates. Due to its great potency, it must be handled with greater precautions than other substances. Because fentanyl and other drugs can harm people based on exposure, many harm reduction agencies and law enforcement agencies are attempting to develop methods and procedures to presumptively and safely identify drugs without risk to the person collecting, confiscating, or testing these drugs.

First responders are trained to use the opioid antagonist naloxone, which is the treatment of choice to reverse the potentially fatal respiratory depression caused by opioid overdose. First responders arriving at a scene of a suspected drug overdose, law enforcement officers searching an area for illicit drugs, or medical professionals performing overdose reversal treatment, are often at risk of being exposed to toxic substances such as heroin, fentanyl, carfentanil, or other synthetic or non-synthetic opioids. Accidental exposure can occur under a number of circumstances, including during the execution of search or arrest warrants, the purchase of opioids during undercover operations, the processing of drug evidence, or the processing of non-drug evidence (e.g., drug proceeds, pill presses, scales, or drug paraphernalia) which may be contaminated with opioids.

There are many different methods and techniques already in use to identify unknown substances. These include instrumentation methods as well as presumptive color tests. A variety of analytical techniques have been used in forensic laboratories for the comprehensive screening of opioids. Analysis techniques for confirmatory and quantitative assays of these drugs are based on immunoassay (such as ELISA) or chromatography (GC-MS, LC-MS, SFC-MS) Immunoassay based detection is rapid, but the main drawback is poor selectivity. In fact, immunoassay based techniques fail to identify the majority of opioids due to the wide structural variety of the targets. In contrast, GC-MS and LC-MS are robust and reliable techniques for qualitative and quantitative assays. However, making them robust enough for use in field settings is very challenging. They require consumable supplies, regular maintenance, power, trained operators, and repair staff—a whole technological infrastructure which may not be available in the field. These types of instruments may be better suited in a field laboratory setting where they can be used for confirmatory analyses.

There are several types of hand-held spectrometers which can be deployed to do fast, qualitative screening under field conditions. Different types of handheld devices have different strengths and weaknesses. For example, Raman spectrometers can often acquire spectra through a plastic bag or glass container, so the operator does not need to come in contact with the sample. However, fluorescence from impurities or cutting agents can prevent matching of the sample to a library spectrum. This is a particular problem for raw heroin, and surface-enhanced Raman substrates may be required to ensure that the signal from the heroin can be detected. Also, all handheld spectrometers require extensive libraries of sample spectra, and many do not analyze mixtures well. Furthermore, handheld spectrometers require a hefty capital investment and must be maintained and calibrated.

There are also currently several different presumptive tests to identify illicit drugs. These include the Marquis test and the Duquenois-Levine test, among others. These tests rely on color changes that occur in the presence of certain controlled substances and functional groups present in chemical compounds. However, given that many drugs are "cut" with other substances, color tests can be subject to false positives and false negatives. Common cutting agents for cocaine include diphenhydramine, caffeine, levamisole, benzocaine, lactose, and mannitol. Diphenhydramine, lactose, mannitol, and even fentanyl are also common cutting agents seen in heroin samples. These cutting agents can produce color changes similar to those seen by controlled substances when tested using presumptive color tests. Some cutting agents such as caffeine, quinine, and diphenhydramine have been shown to give false-positive color tests for other substances. Therefore, these substances may lead to the assumption that a controlled substance is present in a sample when there may be no controlled substance at all.

Previous studies involving color tests have mainly focused on determining which compounds react to give a color change. These studies have not extensively studied mechanisms of color change or extensively tested various mixtures in the study design. While it is important to know which compounds react with color tests, it is also important to understand the effects that cutting agents can have on these tests, as many confiscated drug samples are cut with different compounds. Conventional color tests (e.g., Marquis) also use strong acids such as sulfuric acid, which can present a danger to the tester.

Several companies have developed kits that enable specific chemical color tests to be performed outside a lab setting. A given kit detects members of one chemical class, e.g., narcotics, but not amphetamines. Kits often include hazardous materials such as concentrated sulfuric acid and heavy metals, or contain glass ampoules that must be broken by the operator. Kits include multiple manipulations of the sample and kit materials that must be carried out correctly. Furthermore, they can give ambiguous or uninterpretable results if performed incorrectly or when the illicit substances are impure or adulterated with cutting agents.

Given the above, there is a need in the art for new and improved materials and methods for testing for the presence of opioids such as fentanyl. Due to the prevalence of fentanyl being on the rise, combined with the harmful effects associated with fentanyl, there is a need to be able to identify fentanyl quickly and safely in a field setting. There is also a need to be able to detect opioids in the presence of cutting agents.

SUMMARY

Provided is a testing assay comprising a substrate having a first area with Eosin Y thereon and a second area having cobalt thiocyanate thereon.

In certain embodiments, the substrate is a fabric. In certain embodiments, the substrate is a non-woven fabric. In certain embodiments, the substrate comprises polyester, polypropylene, nylon, cotton, cotton blends, wood pulp, polyurethane foam, or rayon fibers.

In certain embodiments, the substrate is paper. In certain embodiments, the substrate comprises nitrocellulose. In certain embodiments, the substrate comprises cardboard.

In certain embodiments, the first area has Eosin Y at a first pH thereon, and the substrate further comprises a third area having Eosin Y at a second pH thereon. In particular embodiments, the first pH is 5 and the second pH is 7.

In certain embodiments, the testing assay is in the form of a wipe having the first area comprising Eosin Y and the second area comprising cobalt thiocyanate. The first area may be dipped or soak in Eosin Y, and the second area may be dipped or soaked in cobalt thiocyanate.

In certain embodiments, the first area comprises Eosin Y and phosphotungstic acid. In certain embodiments, the first area comprises Eosin Y aggregates created with 0.02% w/w Eosin Y and 0.02% w/w phosphotungstic acid in a citrate or phosphate buffer. In certain embodiments, the first area comprises Eosin Y aggregates created with from 0.005% w/w to 0.2% w/w Eosin Y and from 0.005% w/w to 0.5% w/w phosphotungstic acid in a citrate or phosphate buffer. In certain embodiments, the first area comprises Eosin Y in water at a concentration of 0.02% w/w. In certain embodiments, the first area comprises Eosin Y in water at a concentration of from 0.01% w/w to 0.1% w/w.

Further provided is a wipe for testing for opioids, the wipe comprising a fabric substrate comprising Eosin Y. In certain embodiments, the Eosin Y comprises Eosin Y aggregates created with 0.02% w/w Eosin Y and 0.02% w/w phosphotungstic acid in a citrate buffer. In certain embodiments, the wipe comprises Eosin Y in water at a concentration of 0.02% w/w. In certain embodiments, the wipe has a color contrast ratio (CCR) greater than 1.2. In certain embodiments, the wipe has a CCR greater than 1.5. In certain embodiments, the wipe has a CCR greater than 2.0. In certain embodiments, the wipe exhibits a color change upon contacting an opioid. In particular embodiments, the color change can be used to indicate the presence of fentanyl and fentanyl analogs at a concentration of 0.01% or higher. In particular embodiments, the color change occurs in the presence of fentanyl and fentanyl analogs, but not in the presence of cocaine, heroin, methamphetamine, or 3,4-methylenedioxymethamphetamine (MDMA, also referred to as ecstasy).

Further provided is a method for detecting the presence of an opioid, the method comprising contacting an unknown substance with a wipe comprising Eosin Y in a first area, wherein a color change in the first area from orange to pink indicates that the unknown substance is likely, or likely contains, an opioid. In certain embodiments, the wipe comprises a fabric substrate comprising Eosin Y. In certain embodiments, the wipe comprises Eosin Y aggregates created with 0.02% w/w Eosin Y and 0.02% w/w phosphotungstic acid in a citrate buffer. In certain embodiments, the wipe comprises Eosin Y in water at a concentration of 0.02% w/w. In certain embodiments, the wipe further comprises cobalt thiocyanate in a second area.

Further provided is a method for detecting the presence of an opioid, the method comprising contacting a test strip with an unknown substance, wherein the test strip has Eosin Y deposited on a first area thereof and cobalt thiocyanate deposited on a second area thereof, and immersing the test strip in water, wherein a color change in the first area from orange to pink and a color change in the second area from orange to blue indicates that the unknown substance is likely, or likely contains, an opioid.

In certain embodiments, no color change in the first area and a color change in the second area of from orange to blue indicates that the unknown substance is likely, or likely contains, cocaine. In certain embodiments, a color change in the first area of from orange to pink, and no color change in the second material, indicates that the unknown substance is likely, or likely contains, furanylfentanyl or o-fluorofentanyl. In certain embodiments, the color change can be used to indicate the presence of fentanyl and fentanyl analogs at concentration of 0.01% or higher. In certain embodiments, the color change occurs in the presence of fentanyl and fentanyl analogs, but not in the presence of cocaine, heroin, methamphetamine, or 3,4-methylenedioxymethamphetamine (MDMA, also referred to as ecstasy).

In certain embodiments, the opioid is fentanyl or a fentanyl analogue. In particular embodiments, the fentanyl or fentanyl analogue is selected from the group consisting of fentanyl, benzylfentanyl, furanylfentanyl, o-fluorofentanyl, NPP, N,N-dimethylaniline, methadone, diphenhydramine, and quinine. In particular embodiments, the fentanyl or fentanyl analogue comprises fentanyl in an amount of at least 0.1% by weight. In particular embodiments, the unknown substance comprises an opioid and further comprises a cutting agent. In particular embodiments, the cutting agent is selected from the group consisting of oxycodone, methadone, morphine, methamphetamine, cocaine, diazepam, boric acid, lactose, mannitol, levamisole, quinine, lidocaine, diphenhydramine, and caffeine.

In certain embodiments, the unknown substance comprises fentanyl or a fentanyl analogue and further comprises a cutting agent. In particular embodiments, the cutting agent is selected from the group consisting of oxycodone, methadone, morphine, methamphetamine, cocaine, diazepam, boric acid, lactose, mannitol, levamisole, quinine, lidocaine, diphenhydramine, and caffeine.

Further provided is a system for testing unknown substances, the system comprising a testing assay comprising a paper substrate having at least two lanes, wherein a first of the at least two lanes comprises Eosin Y and a second of the at least two lanes comprises cobalt thiocyanate; and an application for a smart device configured to read and interpret a result from using the testing assay to test an unknown substance for the presence of an opioid. In certain embodiments, the application includes a calibration mode and a testing mode. In certain embodiments, the application is configured to store test results in a cloud-based database.

Further provided is a kit for testing unknown substances, the kit comprising a first container housing a first substrate material having Eosin Y thereon, and a second container housing a second substrate material having cobalt thiocyanate thereon. The first substrate material and the second substrate material may be the same or different.

Further provided is the use of the combination of Eosin Y and cobalt thiocyanate to screen substances for the presence of an opioid. In certain embodiments, the opioid comprises fentanyl or a fentanyl analogue.

Further provided is a testing assay comprising a substrate comprising Eosin Y. In certain embodiments, the substrate is a fabric. In certain embodiments, the substrate is a paper. In certain embodiments, the testing assay is in the form of a wipe that is configured to change colors upon contact with an opioid. In certain embodiments, the testing assay is in the form of a test strip that is configured to change colors upon immersion in water following contact with an opioid. In certain embodiments, the testing assay comprises a fabric substrate comprising Eosin Y aggregates formed from Eosin Y and phosphotungstic acid in a phosphate or citrate buffer. In certain embodiments, the testing assay comprises a fabric substrate comprising Eosin Y aggregates formed from 0.02% w/w Eosin Y and 0.02% phosphotungstic acid in a citrate or phosphate buffer. In certain embodiments, the testing assay is a wipe having a CCR of greater than 1.2. In certain embodiments, the testing assay is a wipe having a CCR of greater than 1.5. In certain embodiments, the testing assay is a wipe having a CCR of greater than 2.0.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7C shows a photograph of the Eosin Y test strip showing the color change.

FIG. 8A shows the testing card. FIG. 8B shows the testing card being dipped in water after the unknown substance has been swiped across the testing card. FIG. 8C shows color changes developing on the testing card after being dipped in water.

DETAILED DESCRIPTION

Figure 1A:
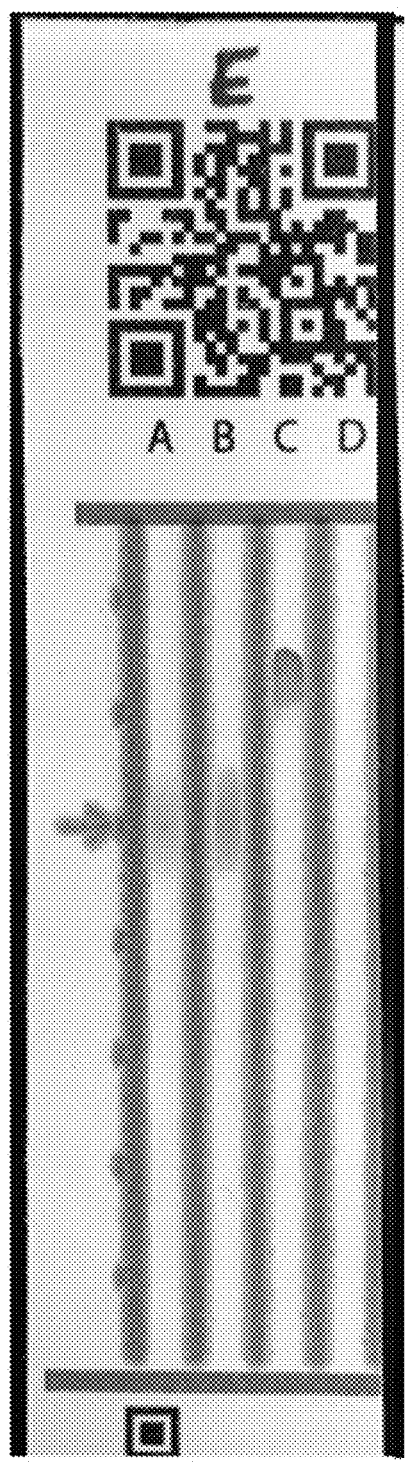
FIG. 1: Photographs of non-limiting example Eosin Y (FIG. 1A) and cobalt thiocyanate (FIG. 1B) test strips.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Simple colorimetric tests (also referred to as "spot tests") for opioids offer speed, simplicity of operation, portability, and affordability. These tests allow first responders to triage samples for additional drug analysis, and provide quick answers to law enforcement officers in the field. Known spot tests include the Marquis, Duquenois-Levine, and Scott tests, which utilize an array of reagents with various handling requirements. Provided herein are improved colorimetric tests that may be utilized in the form of a testing card or other paper substrate-based testing assay, or in the form of a fabric-based testing assay such as a wipe. In some embodiments, the colorimetric tests combine multiple color tests to identify substances. Using multiple color tests allows a user to narrow down which controlled substance is present compared to just using a single color test, as multiple drugs will react or not react with different color tests. Previous tests with multiple colorimetric tests have primarily used the color tests in a liquid assay form. However, multiple color tests can be spotted or printed on a substrate and used in a different fashion.

In accordance with the present disclosure, either Eosin Y or the combination of Eosin Y and cobalt thiocyanate provide useful colorimetric tests for opioids, including when opioids are in mixtures with cutting agents. The term "opioid" is used herein to refer to all drugs with opium-like effects, including opiates such as morphine, codeine, and thebaine (which are directly derived from opium), opioids derived from morphine such as heroin, hydrocodone, and oxycodone, and synthetic opioids such as fentanyl and methadone. The testing assays can detect a wide variety of opiates and synthetic and natural opioids. The testing assays can further identify opioids mixed with commonly used cutting agents, such as caffeine, and can also distinguish mixtures of opioids and cutting agents. A major drawback currently is the exposure of human personnel to the narcotic powder. However, the present disclosure reduces human exposure by providing color-based testing assays.

Eosin Y is a form of eosin, which is a family of fluorescent acidic compounds that bind to and form salts with basic, or eosinophilic, compounds such as proteins containing amino acid residues such as arginine and lysine, staining them dark red or pink as a result of the actions of bromine on fluorescein. Eosin Y, which is also known as 2',4',5',7'-tetrabromofluorescein, has the following structural formula (I):

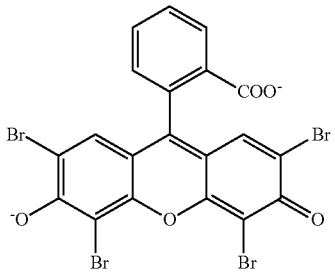

(I)

Eosin Y is a useful as a color test for detecting illicit drugs. Eosin Y has previously been shown to react with hydromorphone, fentanyl, and cocaine, resulting in a purple or pink color change depending on the chemical structure of the interacting agent. The structure of Eosin Y binding to another drug, fluvoxamine, has also been postulated. The binding of fluvoxamine is believed to be based on a primary amine binding with an oxygen group on Eosin Y.

As shown in the examples herein, a variety of drugs of abuse and fentanyl analogues were tested to determine which drugs bind to Eosin Y, which functional groups are capable of binding and eliciting a color change, and a mechanism for Eosin Y binding to fentanyl. Further, opioids were combined with common cutting agents and other drugs of abuse in order to determine the fentanyl detection limit in a drug mixture using an Eosin Y testing assay.

Cobalt thiocyanate, which has the formula $Co(SCN)_2$, is currently used in the cobalt thiocyanate test, also known as the Scott test, for detecting cocaine. The cobalt thiocyanate test has been shown to react with tertiary protonated amines causing a blue color change when interacting with cocaine or fentanyl. It is believed that cocaine binds in a 2:1 ratio with cobalt thiocyanate to produce a blue color change. The addition of cobalt thiocyanate to cocaine hydrochloride results in the surface of the particles turning a bright blue (or a faint blue for cocaine base). The solution changes back to pink upon addition of hydrochloric acid. The addition of chloroform results in a blue organic layer for both cocaine hydrochloride and cocaine base. However, diphenhydramine and lidocaine also give blue organic layers, resulting in false positives for cocaine using the Scott test.

Cobalt thiocyanate was used in the examples herein to demonstrate that the combination of cobalt thiocyanate and Eosin Y is useful to identify opioids such as fentanyl. Through the testing performed, it can be concluded that (1) Eosin Y is capable of detecting low amounts of fentanyl down to 1%; (2) Eosin Y binds to select tertiary amines to produce an orange to pink color change; and (3) Eosin Y binds to the non-piperidine ring nitrogen of fentanyl as a primary binding site and the piperidine ring nitrogen as a secondary binding site. While the cobalt thiocyanate assay detected 1% fentanyl in some of the mixtures, Eosin Y detected 1% fentanyl in all of the mixtures. Based on these results, Eosin Y is useful to screen for fentanyl and fentanyl analogues, and can detect fentanyl in low amounts when mixed with common cutting agents. A testing assay with an Eosin Y test combined with a cobalt thiocyanate test provides for enhanced accuracy in detecting opioids.

Figure 3:
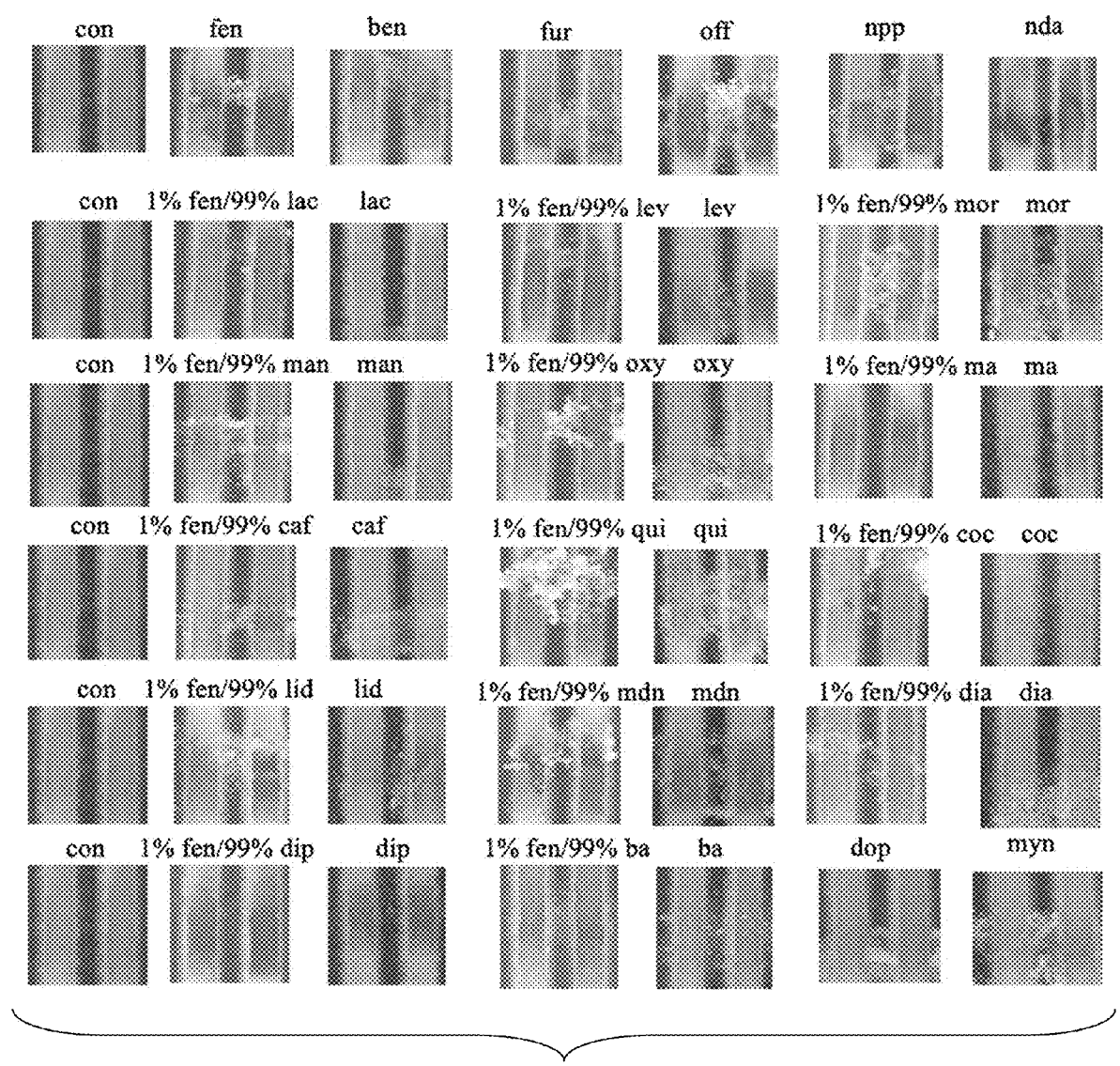
FIG. 3: Eosin Y test results from compounds and mixtures tested in the examples herein. The left lane in each picture contains the Eosin Y test at a pH of 5, and the right lane in each picture contains the Eosin Y test at a pH of 7. Abbreviations correspond in the following way: Con=control, Fen=fentanyl, Ben=benzylfentanyl, Fur=furanylfentanyl, Off=o-fluorofentanyl, Npp=N-phenethyl-4-piperidinone, Nda=N,N-dimethylaniline, Lac=lactose, Lev=levamisole, Mor=morphine, Man=mannitol, Oxy=oxycodone, Ma=methamphetamine, Caf=caffeine, Qui=quinine, Coc=cocaine, Lid=lidocaine, Mdn=methadone, Dia=diazepam, Dip=diphenhydramine, Ba=boric acid, Dop=dopamine, Myn=methylone.
Figure 4:
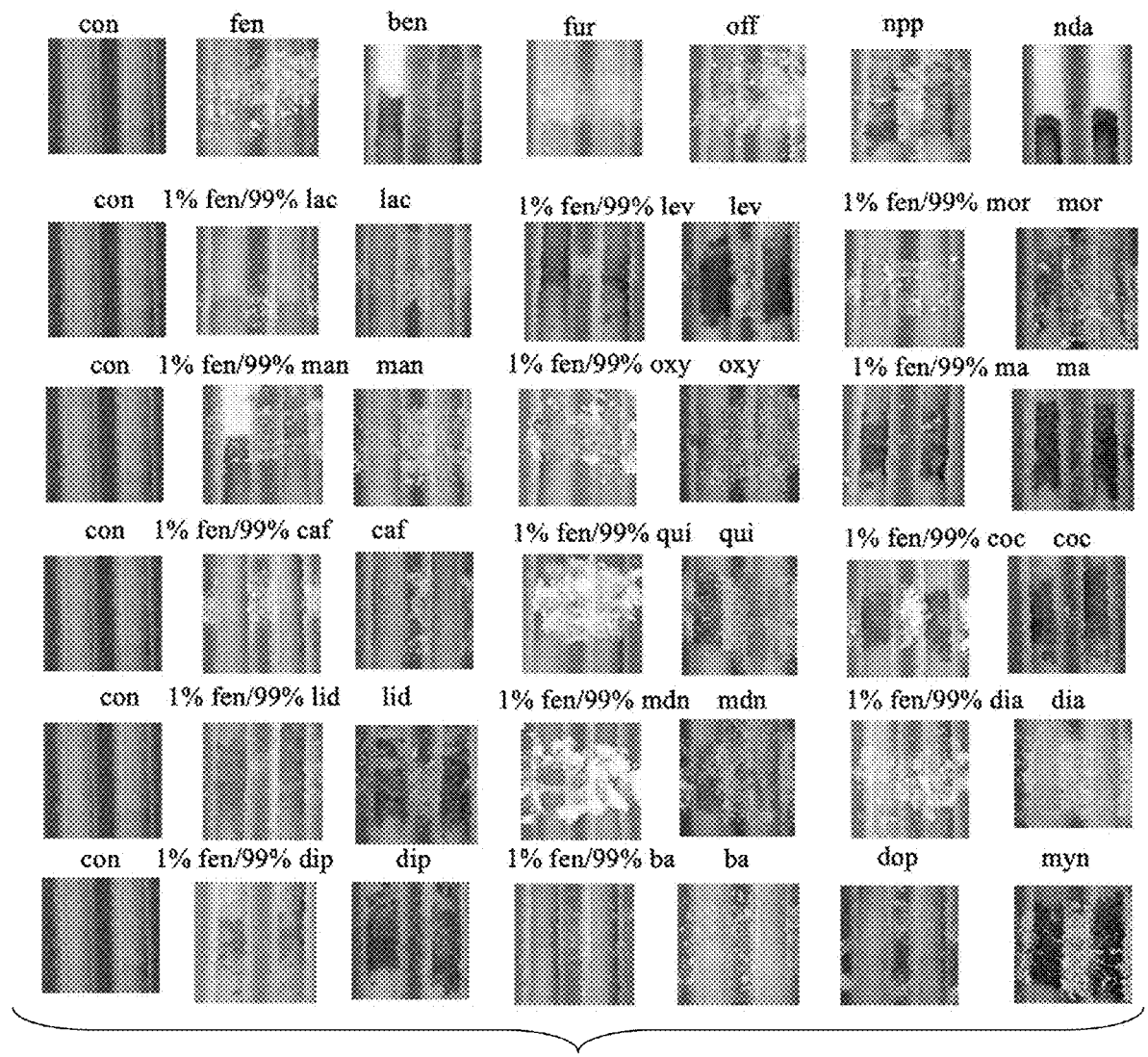
FIG. 4: Cobalt thiocyanate test results from compounds and mixtures tested in the examples herein. The left lane in each picture contains the cobalt thiocyanate test in tosic acid, and the right lane in each picture contains the cobalt thiocyanate test in Tris buffer at a pH of 8. Abbreviations correspond in the following way: Con=control, Fen=fentanyl, Ben=benzylfentanyl, Fur=furanylfentanyl, Off=o-fluorofentanyl, Npp=N-phenethyl-4-piperidinone, Nda=N,N-dimethylaniline, Lac=lactose, Lev=levamisole, Mor=morphine, Man=mannitol, Oxy=oxycodone, Ma=methamphetamine, Caf=caffeine, Qui=quinine, Coc=cocaine, Lid=lidocaine, Mdn=methadone, Dia=diazepam, Dip=diphenhydramine, Ba=boric acid, Dop=dopamine, Myn=methylone.

Furthermore, the multiple color tests (i.e, tests using both Eosin Y and cobalt thiocyanate, separately) can be used to narrow down which controlled substance is present. As seen in FIGS. 3-4, for example, Eosin Y produces a negative result for cocaine, but cobalt thiocyanate produces a positive result for cocaine. Thus, an unknown substance that produces a positive cobalt thiocyanate test and a negative Eosin Y test may be cocaine, and is not likely to be fentanyl or a fentanyl analogue (which produce strong positive Eosin Y results, as shown in FIG. 3). Additionally, as seen in FIGS. 3-4, Eosin Y produces a positive result for the fentanyl analogues furanylfentanyl and fluorofentanyl, but cobalt thiocyanate produces a negative result for these fentanyl analogues. Thus, an unknown substance that produces a positive Eosin Y test and a negative cobalt thiocyanate test may be furanylfentanyl or o-fluorofentanyl.

In some embodiments, a testing assay comprising Eosin Y and cobalt thiocyanate is provided. Eosin Y and cobalt thiocyanate may be on the same substrate (e.g., different areas of the same strip of paper, or different sides or areas of the same wipe) or on different substrate materials (e.g., multiple strips of paper or multiple wipes) in the same kit. The testing assay may include both Eosin Y and cobalt thiocyanate coated or deposited on separate areas of a substrate, or, alternatively, the testing assay may include only one of Eosin Y or cobalt thiocyanate coated or deposited on a substrate. The composition of the substrate may depend on the desired application. For example, the substrate may be a paper substrate to form test strips, or the substrate may be a fabric substrate, as discussed in more detail below, for the testing assay to be in the form of a wipe.

In some embodiments, when the substrate is a paper substrate, a testing assay may include a paper substrate with at least a first area having Eosin Y deposited or coated thereon and a second area having cobalt thiocyanate deposited or coated thereon. Though the terms "deposited" or "coated" are used, it is understood that areas of the substrates may simply be soaked in Eosin Y and cobalt thiocyanate. As another alternative, the Eosin Y and/or cobalt thiocyanate may be printed on the substrate. Alternatively, multiple strips of paper, each having only one of Eosin Y and cobalt thiocyanate thereon, may be provided in a combined configuration. One or more lanes on each strip of paper may be soaked in one of Eosin Y or cobalt thiocyanate. The paper substrate may include, for example, nitrocellulose, cardboard, or any paper-based material. However, other paper substrate materials are possible and are entirely encompassed within the scope of the present disclosure. Printing paper test strips can be used as a safer alternative to conventional tests which use strong acids such as sulfuric acid, as the chemicals on the paper test strips have already dried by the time they are used.

Figure 8A:
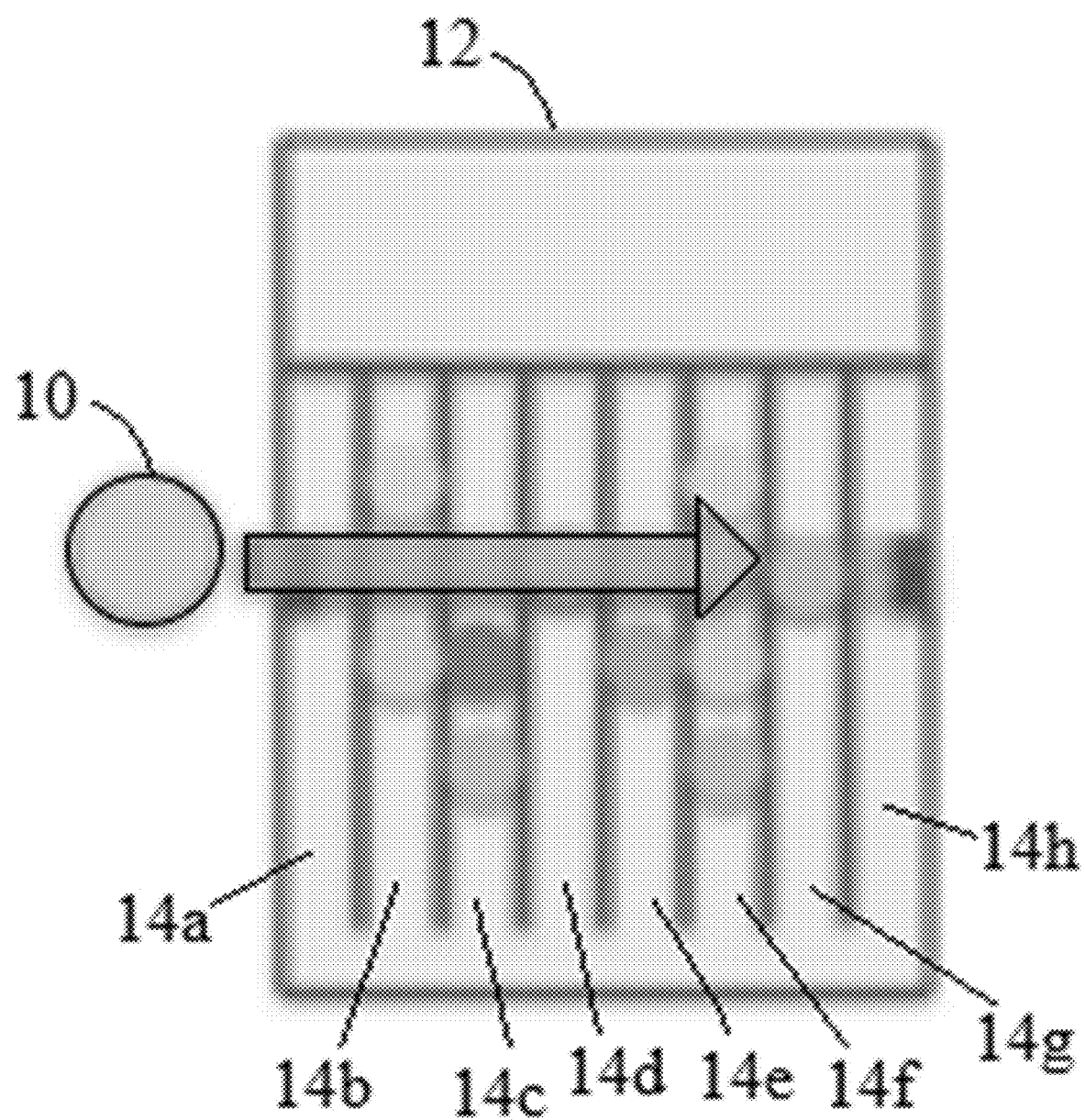
FIGS. 8A-8C: Illustrations of a testing card and a method of using the same to test an unknown substance for the presence of an opioid.
Figure 8B:
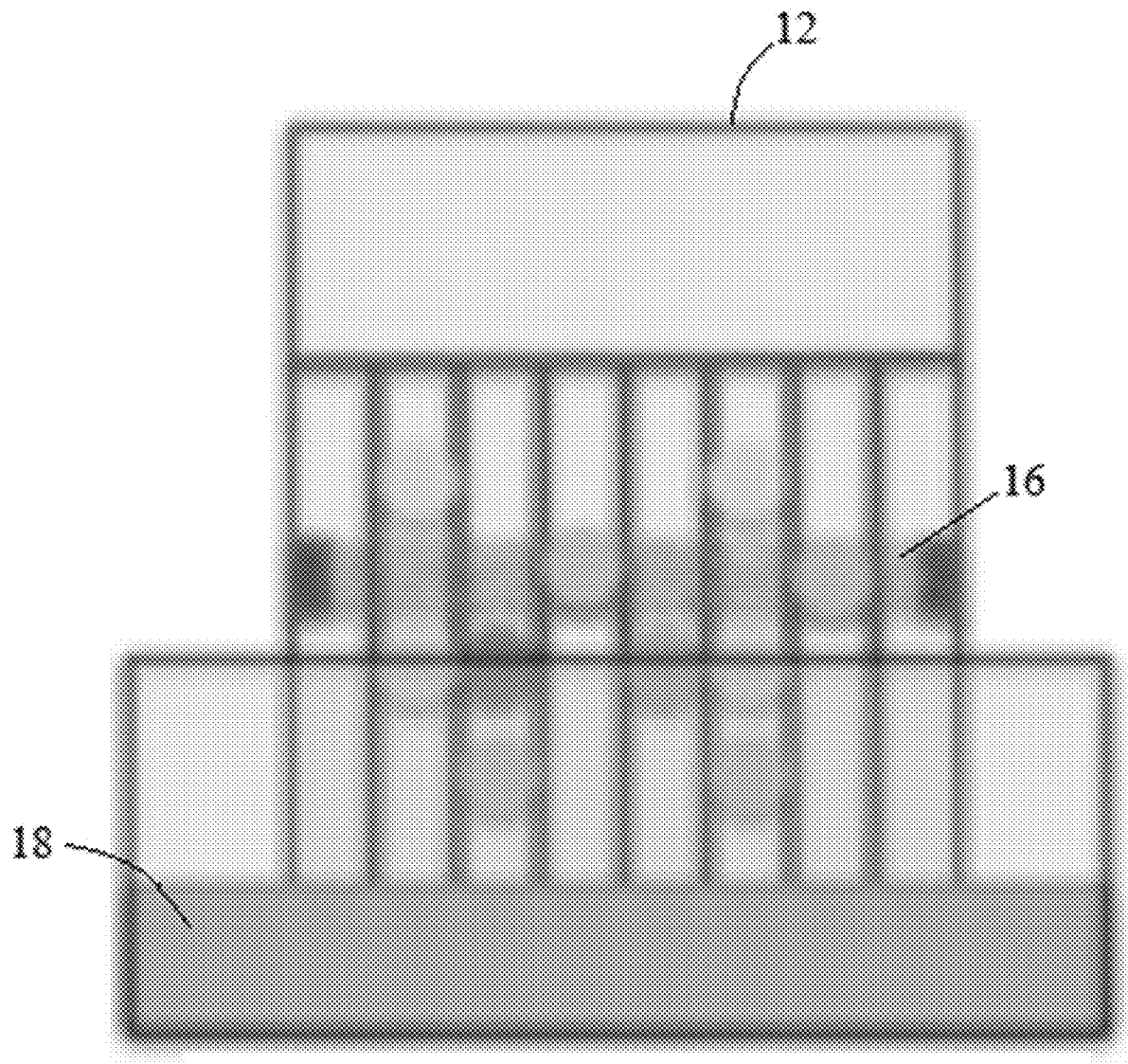
Figure 8C:
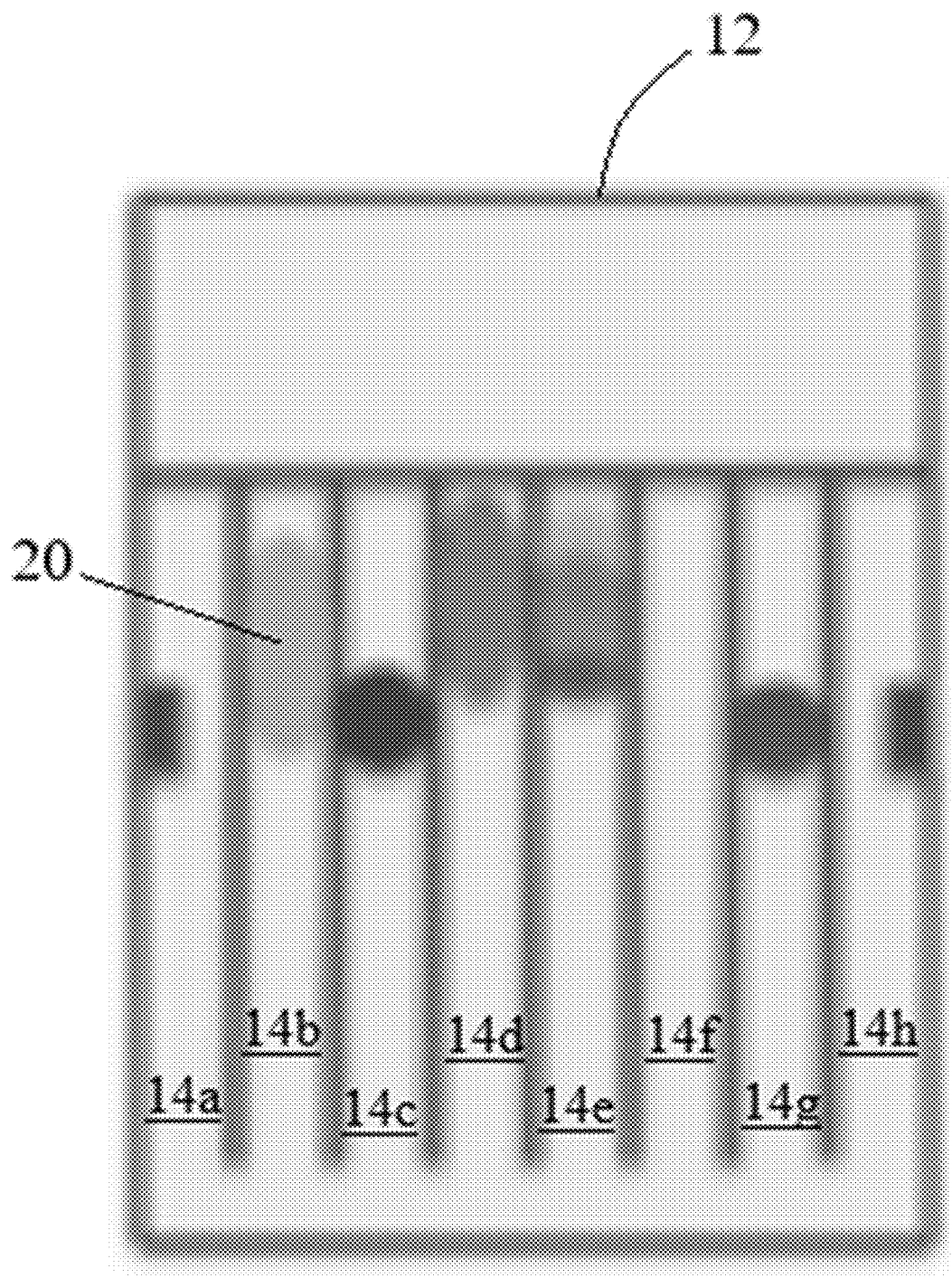

In some embodiments, the testing assays provided herein may be in the form of a testing card that is about the size of a playing card, and may contain twelve lanes, each loaded with reagents that carry out different chemical analyses. Such testing cards may be used for the colorimetric detection of illicit narcotics. Referring now to FIGS. 8A-8C, provided herein is a testing assay in the form of a paper testing card 12 with colorimetric chemistries that produce a visible optical change in the presence of opioids. The color change is based on the reaction of functional groups of opioids with spotted chemistries on the paper testing cards 12. Each paper testing card 12 may include a plurality of lanes 14a-14h, which allows for several pre-determined reactions to take place within the same testing card 12, and allows for accurate multiplexed detection. In one non-limiting example, the testing card 12 includes only two lanes: a first lane soaked in Eosin Y and a second lane soaked in cobalt thiocyanate. In other embodiments, the testing card 12 includes more lanes, such as the twelve lanes 14a-14h depicted in FIGS. 8A-8C. In such embodiments, more than one lane may be soaked in Eosin Y or cobalt thiocyanate, for example at different pHs or different concentrations of Eosin Y or cobalt thiocyanate. Additionally, one or more of the lanes 14a-14h may include a control having no reagent therein, or may include additional reagents known to produce color changes in the presence of opioids or other illicit substances.

Referring still to FIGS. 8A-8C, a first step for using the testing card 12 may be to apply the unknown substance, such as a powder 10, to the testing card 12 such that each lane 14a-14h is exposed to the powder 10. This may be accomplished, for example, by smearing or swiping the powder 10 across the testing card 12, as depicted with the arrow in FIG. 8A. The powder 10 to be tested is scraped across all twelve lanes 14a-14h of the paper testing card 12 in order to deposit a few milligrams of material in each lane 14a-14h. If the unknown substance is encapsulated in a protective polymer, such as a protective polymer used to protect first responders from exposure, then the protective polymer may be removed prior to testing. The smearing or swiping of the powder 10 may leave a powdered area 16 across each of the lanes 14a-14h of the testing card 12. As shown in FIG. 8B, the testing card 12 may then be dipped in water 18 for 1-2 minutes. The water 18 does not need to contact the powdered area 16 because the water 18 will be wicked up by capillary action. For example, the bottom edge of the testing card 12 can be dipped in a dish of water 18. Furthermore, the water 18 does not need to be pure. Water wicks up the twelve lanes 14a-14h and chemical reactions create different colors at the top of the twelve lanes 14a-14h according to the contents of the powder 10. This approach involves capillary wicking of the powder of interest that separates the powder constituents based on their molecular weight and allows differentiation of mixtures. As shown in FIG. 8C, colors 20 may develop in the lanes 14a-14h on the testing card 12 in about 2 minutes, in areas above the powdered area 16 relative to where the lanes 14a-14h were exposed to the water 18.

The color change is reliant on changes in absorption as opposed to emission, and therefore can be read by humans or a simple cell-phone based application, in which centralized data storage and data sharing are possible. Users can be trained to read the testing cards directly, but they can also capture the image of the testing card with a cell phone camera, allowing the raw data from the test to be read by an image analysis program or a trained reader. The entire testing process may be completed in as little as about 5 minutes. Furthermore, the testing cards may include polymer trappers at appropriate locations that can localize expected signals at particular locations in the testing card, and allow for the differentiation between primary, secondary, and tertiary functional groups in the opioid powder of interest.

Because the process of "reading" any visual output is subjective and prone to error, image recognition software can be utilized to make the testing cards more scalable. The testing cards may contain fiducial marks and a QR code which the software recognizes; this enables detection of the testing cards in stored images, as well as geometrical correction of tilted or keystoned images, and can be incorporated into a smart device application. It is possible to store the data from the mobile application in a cloud-based database, which can then be used for verification and validation purposes.

Figure 9:
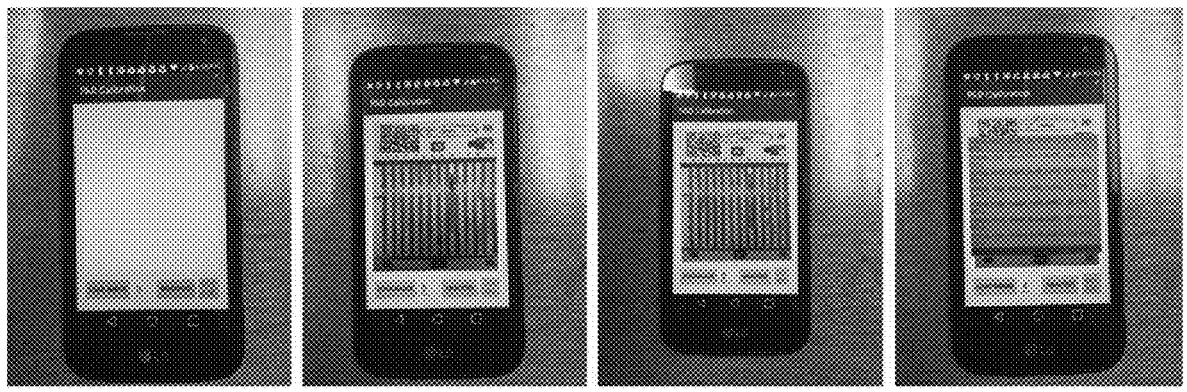
FIG. 9: Photographs of testing card calibration and analysis software on an Android phone.
Figure 10:
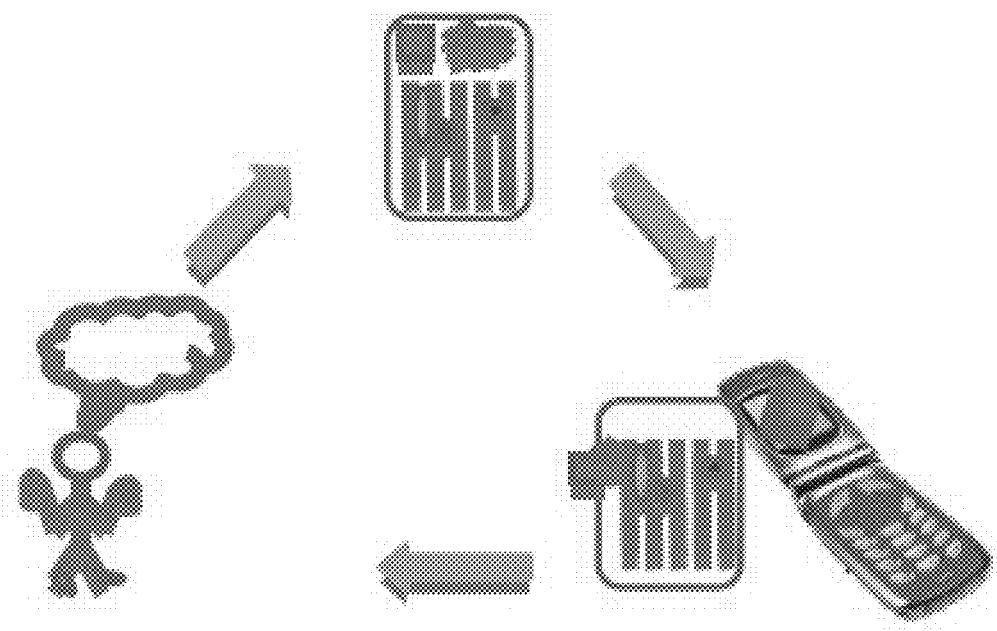
FIG. 10: Illustration of a non-limiting example system for testing unknown substances.

A mobile application may include two software applications. The first is a calibration software which is meant for calibration purposes using testing cards run with known compounds. The second is the analysis software which is configured for testing whether the color on the lanes from an unknown powder sample correspond to any of the reference standards. FIG. 9 shows photographs of testing cards calibration and analysis software on an Android phone. FIG. 10 illustrates a system for testing unknown substances that includes testing cards and an application for a smart device configured to store, read, interpret, and display the testing results.

Figure 21:
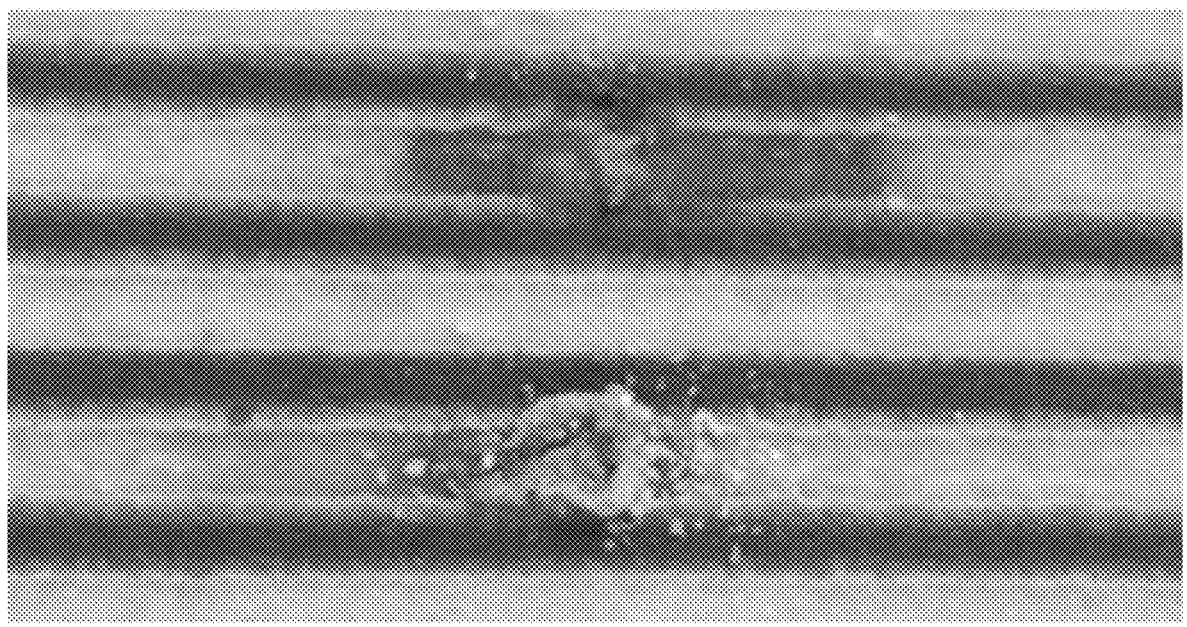
FIG. 21: Photograph of a positive and negative test with Eosin Y on a test strip. The upper lane shows a positive test demonstrated with a fentanyl stimulant. The lower lane shows a negative test with 4-dimethylaminobenzaldehyde. The color change is more dramatic with actual fentanyl.

In other embodiments, provided herein is a wipe comprising Eosin Y, or comprising a combination of Eosin Y and cobalt thiocyanate in different areas. Some or all of the wipe may be saturated in a low concentration solution of Eosin Y in water, or may include Eosin Y aggregates. As discussed above, Eosin Y is a highly selective and sensitive dye, and is an appealing option for a wipe. Eosin Y is noted for its red/orange to pink color change in the presence of fentanyl and analogs. It is capable of detecting fentanyl even in a 1% mixture with substances including cocaine, methamphetamine, and oxycodone. This sensitivity is advantageous as fentanyl is typically mixed with other drugs at low concentrations due to its extreme potency. As described herein, it has been found that Eosin Y primarily associates with the tertiary amine in the position alpha relative to both the phenyl and piperidine rings in fentanyl and secondarily associates with the tertiary amine in the piperidine ring to produce the color change, providing great selectivity to fentanyl's underlying structure. This selective association allows Eosin Y to test positive with fentanyl, benzyl fentanyl, furanyl fentanyl, and o-fluoro fentanyl, as well as other fentanyl analogs identified in drug samples by the DEA NFLIS including acetyl fentanyl, fluoroisobutyryl fentanyl, valeryl fentanyl, and carfentanil. The test is negative for most drugs with tertiary amines includes oxycodone, heroin, morphine, cocaine, and others. This is illustrated, for example, in FIG. 21, where a color change is seen in the upper lane following contact with a powder containing a fentanyl simulant, and a lack of color change to pink is seen in the lower lane following contact with a powder containing 4-dimethylaminobenzaldehyde. Alternative chemistries may be employed in addition to, or instead of, Eosin Y in the wipe to detect fentanyl or other opioids. For example, Eosin Y may be combined with cobalt thiocyanate on different regions or sides of the same wipe.

A wipe may be composed, for example, of a substrate material with Eosin Y thereon, or with Eosin Y on part of the substrate material and cobalt thiocyanate on another part of the substrate material. Wipes may be made from non-woven fabrics that have been soaked in an Eosin Y solution, or in separate solutions of Eosin Y and cobalt thiocyanate. Suitable substrate materials for the wipes include, but are not limited to, polyester, polypropylene, nylon, cotton, cotton blends, wood pulp, polyurethane foam, or rayon fibers formed into sheets, or combinations thereof, any of which may be moistened with water or other ingredients in addition to the Eosin Y, or in addition to the Eosin Y and cobalt thiocyanate. In one non-limiting example, all of the wipe's surface area has been dipped or soaked in Eosin Y, creating an orange wipe (before contacting a substance that would cause a color change) as seen in the photograph in FIG. 20. In other embodiments, a wipe includes a first region or side having been dipped or soaked in Eosin Y and a second region or side having been dipped or soaked in cobalt thiocyanate.

A wipe can be a colorimetric wipe if the background and foreground have sufficient color contrast for a user to visually discriminate between background and foreground. A quantitative method to quantify the difference in background and foreground color is the Color Contrast Ratio (CCR). CCR is a number between 1 and 21, and can be calculated using the following formula:

$$CCR=(L1+0.05)/(L2+0.05)$$

where L1 and L2 are relative luminance of lighter and darker colors, respectively, such that L1>L2. The relative luminance in turn can be calculated from the RGB values of the background and foreground. For the wipes described herein, it is important that the CCR is >1.2, preferably >1.5, and more preferably >2.0. However embodiments having a lesser CCR are nonetheless encompassed within the scope of the present disclosure.

A low concentration of Eosin Y solution in water may be used to soak a substrate to form a wipe. The substrate may be dipped in the solution, coated in the solution, immersed in the solution, sprayed with the solution, or the solution may otherwise be deposited or printed on the substrate. The concentration of Eosin Y in water in the solution may range from about 0.005% w/w to about 0.2% w/w, or from about 0.01% w/w to about 0.1% w/w. In one non-limiting example, a wipe is dipped in a solution of Eosin Y in water at a concentration of 0.02% w/w.

In another non-limiting example, a wipe comprises Eosin Y aggregates created with 0.02% w/w Eosin Y and 0.02% w/w phosphotungstic acid in a citrate or phosphate buffer. Phosphotungstic acid is a heteropoly acid used in biological staining to precipitate different types of dyes. It has been found that phosphotungstic acid can be used to agglomerate in solution and create aggregates of Eosin Y, which can lead to increased distinction between foreground and background. The result is that the background color of Eosin Y is significantly reduced, which enables better contrast when it interacts with fentanyl. Thus, formulations that include phosphotungstic acid along with Eosin Y provide for easier reading of test results. The phosphotungstic acid can be present in an amount ranging from about 0.005% w/w to about 0.5% w/w.

The wipes may further include other possible additives, including, but not limited to, phosphomolybdic acid, and one or more surfactants such as Tween 20, sodium dodecyl sulfate, and Polysorb 80.

In some embodiments, a wipe includes both Eosin Y and cobalt thiocyanate, for enhanced distinction between fentanyl/fentanyl derivatives and other compounds, such as heroin, cocaine, aspirin, etc. In such embodiments, the wipe may include a first area comprising Eosin Y and a second area comprising cobalt thiocyanate. The first area may be on the first side of the wipe, and the second area may be on the second side of the wipe, but this is not necessary. Rather, in the alternative, the first area may be on the same side of the wipe as the second area. The cobalt thiocyanate may be present at a similar concentration as the Eosin Y, namely, from about 0.005% w/w to about 0.2% w/w, or from about 0.01% w/w to about 0.1% w/w.

To perform a test with a wipe as described herein, the user may simply don gloves, remove the wipe from packaging, and quickly wipe it across a surface containing a suspicious powder or substance. Results will develop instantaneously. The red/orange part of the wipe (coloration from the Eosin Y) turns pink where it contacts fentanyl or analogs in a positive test. If cobalt thiocyanate is included on the wipe, the area comprising cobalt thiocyanate turns blue where it contacts opioids such as fentanyl or cocaine. A coloration guide can be provided to aid in the identification of a positive test. Other chemistries, besides Eosin Y and cobalt thiocyanate, are possible for this test as well, which may also involve a color change. Based on the results, the user can then respond to the powder or substance appropriately and efficiently to maximize safety. In some applications, it is desirable to distinguish fentanyl and fentanyl analogs from other opioids. Since fentanyl is much more dangerous, the response to a fentanyl contamination is much more serious than the response to the presence of other opioids such as cocaine. For example, if a white powder is suspected to contain fentanyl, the area may need to be decontaminated with special decontamination agents and hazardous personnel, given the deadly effect of fentanyl and fentanyl analogs.

The wipes saturated with Eosin Y solution at a low concentration can be safely handled with gloves, and thus do not add to the inherent hazard of an unknown powder or substance being tested. Areas of the wipes that come into contact with a powder or substance being tested can be analyzed for color change to determine the result of the test, possibly with the aid of a coloration guide, though the use of a coloration guide is not strictly necessary. These tests in the field are presumptive in nature and are not designed to replace comprehensive drug tests. Rather, they act as a quick indicator, giving crucial guidance to parties dealing with an unknown powder or substance to ensure an appropriate response and improve safety for involved parties.

The wipes and other testing assays described herein are useful for providing the safe identification of illicit and dangerous substances, such as narcotics. Narcotics such as fentanyl and its analogs can be detected alone or in mixtures with other drugs via a simple chemical test. The test can be easily performed by law enforcement as well as public and private establishments such as casinos, prisons, and others that may encounter illicit substances. The distinction of an Eosin Y test for fentanyl is its simplicity and the lack of additional requisite safety precautions enabling safe use by the public. Various similar chemical tests may be employed. The wipes may be further treated post sample contact, or additional chemistries may be applied to the wipes, in order to provide for a wide range of detection capabilities for diverse dangerous and illicit substances, benefitting a wide variety of industries.

Any of the tests described herein may be implemented as testing instruments in a variety of formats, including, but not limited to, wipes, swabs, strips, and the like. The testing instrument can be packaged ready for use. The user can simply wipe the powder or substance on the testing instrument, and wait a few seconds to observe a color change indicating a positive test or a lack of color change indicating a negative test. Other detection chemistries for fentanyl, fentanyl analogs, and other opioids are also possible.

Advantageously, the systems, testing assays, and methods described herein are cheap and easy to use for first responders, law enforcement agents, medical professionals, crime scene investigators, and anyone else who may wish to determine whether an unknown substance is or includes an opioid. The testing assays are portable, self-contained, easy to use, lightweight, allow for testing of possible drugs in minutes, and require no or minimal external power. A field device that can quickly and reliably test the presence of opioids is a major advancement in field testing. These diagnostic tools are attractive for use in the field, or as a rapid response alternative to more-advanced technologies already used in clinical settings.

Another major advantage of paper-based or fabric-based testing assays is their low barriers to implementation and scaling. Capital investment required is insignificant, training is fast, the tests are easy to use, and the turnaround time is just minutes. Testing cards can be manufactured by a printing technology, or may be manufactured by a roll-to-roll fabrication line on a larger scale at very low cost (<$1 per unit). Similarly, wipes can be manufactured by simply soaking fabric substrates in the Eosin Y solution.

The testing assays may be modified in various ways to suit the needs of first responders, law enforcement agents, and medical professionals. The overall packaging and testing process of the testing assays can also be modified in any manner to reduce the risk of unwanted exposure, as well as to ensure consistent application of unknown powder to the paper testing cards or fabric wipes.

The testing assays and methods described herein can be embodied in the form of a kit or kits. A non-limiting example of such a kit is a kit for testing unknown substances, the kit comprising a substrate material having Eosin Y thereon and a substrate material having cobalt thiocyanate thereon in separate containers, where the containers may or may not be present in a combined configuration. Many other kits are possible, such as kits having a substrate material with Eosin Y at a first pH deposited thereon and a substrate material with Eosin Y at a second pH deposited thereon. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

In the present examples, which illicit drugs and cutting agents react with Eosin Y was evaluated. Additionally, cobalt thiocyanate was used to determine if the combination of cobalt thiocyanate and Eosin Y has the ability to identify fentanyl. Due to the prevalence of fentanyl being on the rise, combined with the harmful effects associated with fentanyl, there is a need to be able to identify fentanyl quickly and safely in a field setting.

Example I—Drug Detection Using Cobalt Thiocyanate and Eosin Y Paper Assays

Materials and Methods

Chemicals Used and Suppliers

The following compounds were obtained from Sigma-Aldrich (St. Louis, MO): boric acid, caffeine, cocaine (hydrochloride salt), diazepam, diphenhydramine (hydrochloride salt), dopamine (hydrochloride salt), lactose, levamisole (hydrochloride salt), lidocaine (hydrochloride salt), mannitol, quinine (sulfate salt), and methadone (±hydrochloride salt). The following compounds were obtained from Cayman Chemical (Ann Arbor, MI): morphine (sulfate hydrate salt), fentanyl (hydrochloride salt), benzylfentanyl(hydrochloride salt), o-fluorofentanyl (hydrochloride salt), furanylfentanyl (hydrochloride salt), methamphetamine (±hydrochloride salt), N-phenethyl-4-piperidinone (NPP), and methylone (hydrochloride salt). The following compound was obtained from Mcule (Palo Alto, CA): N,N-dimethylaniline (hydrochloride salt).

Determining the Compounds that React with Eosin Y

Figure 2:
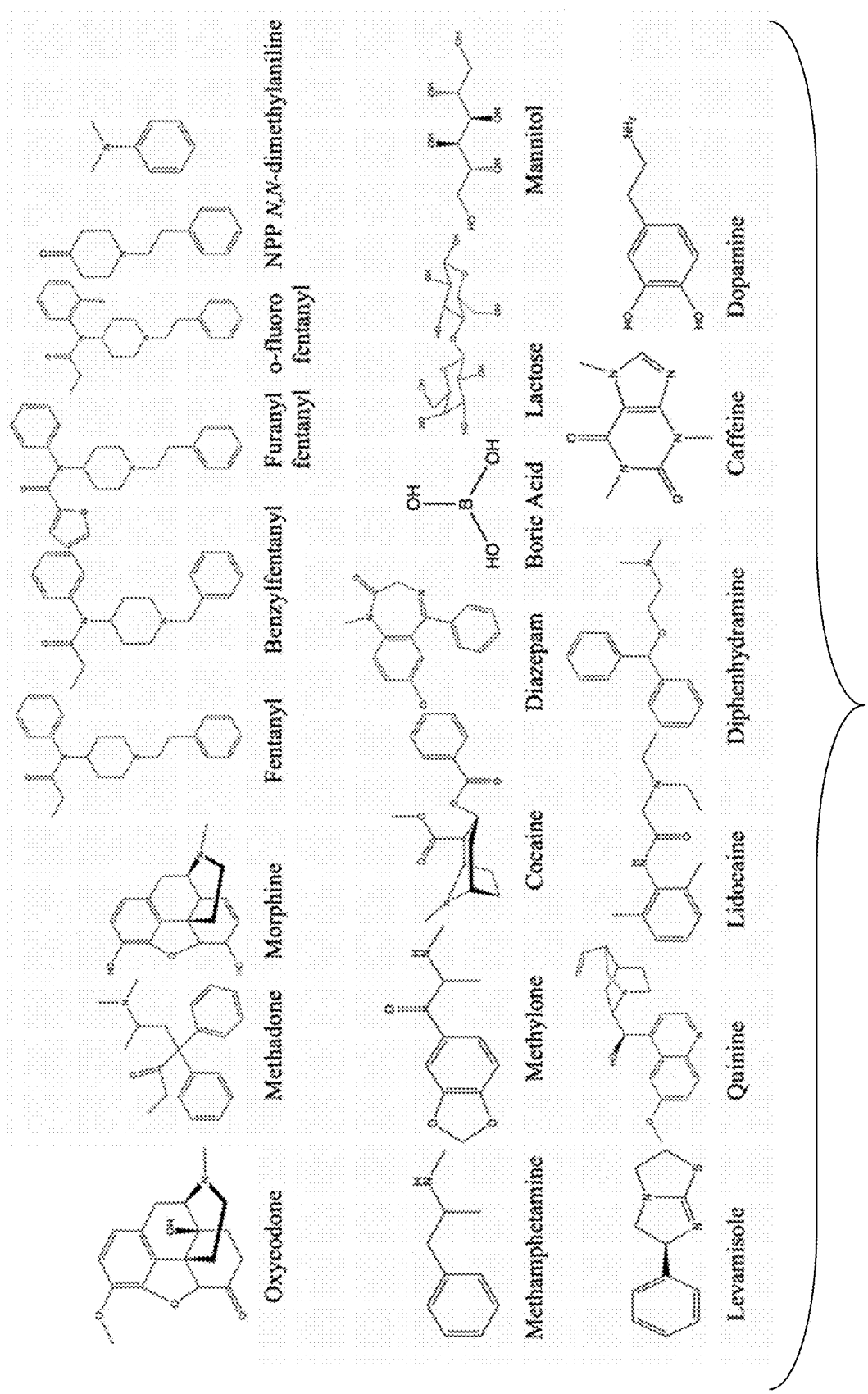
FIG. 2: Structures of compounds tested in the examples herein.

To determine the compounds that react with Eosin Y, Eosin Y paper assay strips were used. These were nitrocellulose strips that had Eosin Y at a pH of 5 and a pH of 7 placed onto them in separate columns. The pH of 5 and 7 were chosen based on the theory that various opioids could be differentiated at two different pHs. These strips were made by Vuronyx Technologies (Woburn, MA). An example of the strip is depicted in FIG. 1A. The following compounds were tested to determine if there was a visible color change: oxycodone, methadone, morphine, fentanyl, benzylfentanyl, furanylfentanyl, o-fluorofentanyl, methamphetamine, methylone, cocaine, diazepam, boric acid, lactose, mannitol, levamisole, quinine, lidocaine, diphenhydramine, caffeine, dopamine, NPP, N,N-dimethylaniline Structures of each compound are depicted in FIG. 2. These compounds were specifically chosen to determine which compounds Eosin Y will react with, based on their chemical structures and functional group substitutions. The most common drugs and cutting agents seen in crime labs were chosen to achieve a variety that would help in narrowing down which functional groups bind to Eosin Y. Given that Eosin Y is believed to react with amine groups, a variety of amine groups were selected to test including primary, secondary, and tertiary amines Approximately 1-2 mg of each compound was deposited on the strip and the strip was immersed in water for 2 minutes for testing. A control was used where no sample was deposited, and the strip was immersed in water for 2 minutes. Each strip was then allowed to dry for 3 minutes before a photograph was taken for comparison. Each strip was compared to the control to determine if a color change occurred. Eosin Y was deemed to be a positive color change if the strip was pink at the sample arrow in comparison to the control which was orange. For a positive response, the pink color obtained had to be similar to the pink color seen with fentanyl alone.

Figure 1B:
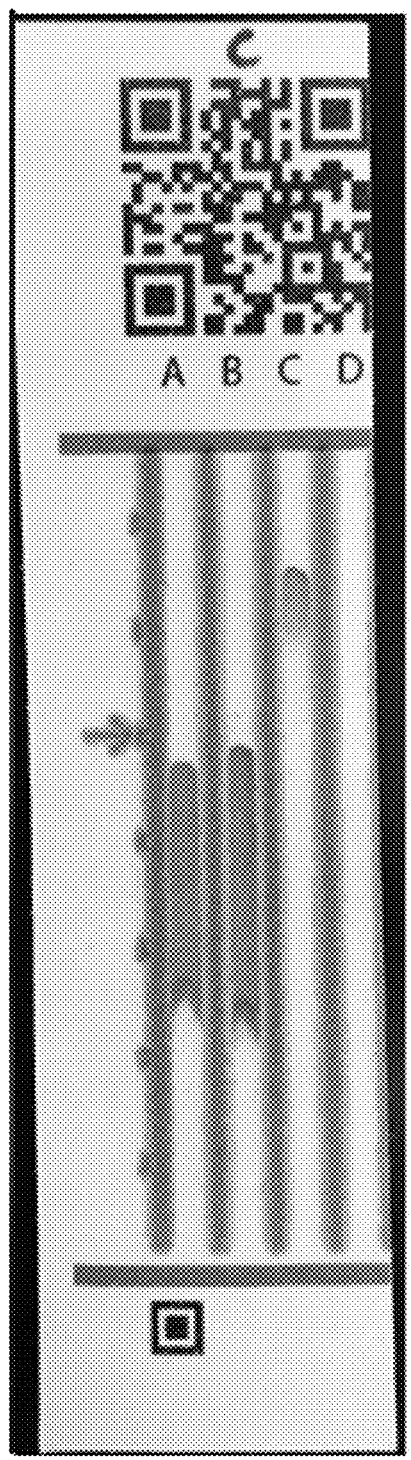

Determining if Cobalt Thiocyanate Used in Conjunction with Eosin Y can Specifically and Uniquely Identify Fentanyl To determine if fentanyl is a unique compound that reacts with Eosin Y and cobalt thiocyanate, Eosin Y and cobalt thiocyanate paper assay strips were used. The cobalt thiocyanate strips contained cobalt thiocyanate with tosic acid in one column and Tris buffer at a pH of 8 in the other column. Most strong acids, such as hydrochloric acid, were found to degrade the paper substrate, except for tosic acid which did not have any detrimental effect on the paper substrate over long term storage. These strips were also made by Vuronyx Technologies (Woburn, MA). An example of the cobalt thiocyanate is depicted in FIG. 1B. The above-mentioned compounds were also tested with the cobalt thiocyanate strips to determine if the compounds would react with cobalt thiocyanate. As with Eosin Y, approximately 1-2 mg of each compound was deposited on the strip and the strip immersed in water for 2 minutes. A control was also used where no sample was deposited, and the strip was immersed in water for 2 minutes. Each strip was then allowed to dry for 3 minutes before a photograph was taken for comparison. Each strip was compared to the control to determine if a color change occurred. Cobalt thiocyanate was deemed to be a positive color change if the strip was blue at the sample arrow in comparison to the control which was red.

Determining the Effects Cutting Agents have on Fentanyl Reacting with Eosin Y Test and Cobalt Thiocyanate To determine if cutting agents would affect fentanyl reacting with both Eosin Y and cobalt thiocyanate, fentanyl was mixed with the following compounds tested above: oxycodone, methadone, morphine, methamphetamine, cocaine, diazepam, boric acid, lactose, mannitol, levamisole, quinine, lidocaine, diphenhydramine, and caffeine. Fentanyl was placed in the mixture at a concentration of 1%, 5%, and 10% with each compound listed above comprising the remaining 99%, 95%, and 90% of the mixture, respectively. Each mixture was then tested with both Eosin Y and cobalt thiocyanate in paper assay form. The testing consisted of each mixture being deposited on the strip and the strip being immersed in water for 2 minutes. Each strip was then allowed to dry for 3 minutes before a photograph was taken for comparison. Note: 10% fentanyl mixtures were not tested for oxycodone, methadone, morphine, methamphetamine, cocaine, and diazepam. The 10% mixtures were not tested when the observation was made that the 1% and 5% mixtures were consistently yielding the same results when reacting with Eosin Y. Each strip was compared to the control to determine if a color change occurred.

Determining a Binding Mechanism for Eosin Y

A mechanism for Eosin Y binding to drugs and eliciting a color change has not yet been established. To determine a mechanism by which Eosin Y binds to fentanyl, fentanyl analogues, and similar compounds were selected based on the substitution of the compound. These include o-fluorofentanyl, benzylfentanyl, furanylfentanyl, NPP, and N,N-dimethylaniline. These compounds were chosen (in order) to determine which of the 2 nitrogens on the fentanyl molecule Eosin Y was binding to based on the interactions between Eosin Y and fluvoxamine believed to occur.

Results

Eosin Y Individual Compound Results

The results for the Eosin Y testing of the individual compounds are listed in Table 1 and depicted in FIG. 3. The control displayed an orange color. Fentanyl, benzyl fentanyl, furanyl fentanyl, o-fluorofentanyl, NPP, N,N-dimethylaniline, diphenhydramine, quinine, and methadone all gave a positive response with Eosin Y turning pink. Lactose, mannitol, caffeine, oxycodone, boric acid, cocaine, dopamine, methylone, and diazepam were all negative with a color matching that of the control. Lidocaine, levamisole, morphine, methamphetamine, and methadone all exhibited color changes but were not the pink color seen with the positive responders. The colors exhibited by these compounds were brighter shades of orange or faded shades of pink which were deemed a negative response. Some of the compounds were difficult to weigh and as a result excess powder can be seen in FIG. 3.

Table 1—Results of Eosin Y and cobalt thiocyanate testing for each compound and mixture along with type of amine in compound. + indicates a pink color change, – indicates no pink color change. NT indicates mixture was not tested. N/A indicates compound does not have an amine functional group.

| Compound | Amine Type | Eosin Y | Cobalt Thiocyanate |
| --- | --- | --- | --- |
| Boric Acid | N/A | – | – |
| Lactose | N/A | – | – |
| Mannitol | N/A | – | – |
| Dopamine | 1° | – | – |
| Methamphetamine | 2° | – | + |
| Methylone | 2° | – | + |
| Lidocaine | 2°/3° | – | + |
| Diphenhydramine | 3° | + | + |
| Caffeine | 3° | – | – |
| Quinine | 3° | + | + |
| Levamisole | 3° | – | + |
| Diazepam | 3° | – | – |
| Methadone | 3° | + | + |
| Oxycodone | 3° | – | + |
| Cocaine HCl | 3° | – | + |
| Morphine | 3° | – | + |
| Fentanyl | 3° | + | + |
| Benzylfentanyl | 3° | + | + |
| O-fluorofentanyl | 3° | + | – |
| Furanylfentanyl | 3° | + | – |
| NPP | 3° | + | + |
| N,N,-dimethylaniline | 3° | + | + |
| 1% Fentanyl/99% Lactose | 3°/N/A | + | – |
| 5% Fentanyl/95% Lactose | 3°/N/A | + | + |
| 10% Fentanyl/90% Lactose | 3°/N/A | + | + |
| 1% Fentanyl/99% Mannitol | 3°/N/A | + | – |
| 5% Fentanyl/95% Mannitol | 3°/N/A | + | – |
| 10% Fentanyl/90% Mannitol | 3°/N/A | + | + |
| 1% Fentanyl/99% Caffeine | 3°/3° | + | – |
| 5% Fentanyl/95% Caffeine | 3°/3° | + | – |

-continued

| Compound | Amine Type | Eosin Y | Cobalt Thiocyanate |
|---|---|---|---|
| 10% Fentanyl/90% Caffeine | 3°/3° | + | + |
| 1% Fentanyl/99% Lidocaine | 3°/2°/3° | + | + |
| 5% Fentanyl/95% Lidocaine | 3°/2°/3° | + | + |
| 10% Fentanyl/90% Lidocaine | 3°/2°/3° | + | + |
| 1% Fentanyl/99% Diphenhydramine | 3°/3° | + | + |
| 5% Fentanyl/95% Diphenhydramine | 3°/3° | + | + |
| 10% Fentanyl/90% Diphenhydramine | 3°/3° | + | + |
| 1% Fentanyl/99% Boric Acid | 3°/N/A | + | − |
| 5% Fentanyl/95% Boric Acid | 3°/N/A | + | − |
| 10% Fentanyl/90% Boric Acid | 3°/N/A | + | − |
| 1% Fentanyl/99% Levamisole | 3°/3° | + | + |
| 5% Fentanyl/95% Levamisole | 3°/3° | + | + |
| 10% Fentanyl/90% Levamisole | 3°/3° | + | + |
| 1% Fentanyl/99% Quinine | 3°/3° | + | − |
| 5% Fentanyl/95% Quinine | 3°/3° | + | + |
| 10% Fentanyl/90% Quinine | 3°/3° | + | + |
| 1% Fentanyl/99% Oxycodone | 3°/3° | + | + |
| 5% Fentanyl/95% Oxycodone | 3°/3° | + | + |
| 10% Fentanyl/90% Oxycodone | 3°/3° | NT | NT |
| 1% Fentanyl/99% Methadone | 3°/3° | + | + |
| 5% Fentanyl/95% Methadone | 3°/3° | + | + |
| 10% Fentanyl/90% Methadone | 3°/3° | NT | NT |
| 1% Fentanyl/99% Morphine | 3°/3° | + | + |
| 5% Fentanyl/95% Morphine | 3°/3° | + | + |
| 10% Fentanyl/90% Morphine | 3°/3° | NT | NT |
| 1% Fentanyl/99% Methamphetamine | 3°/2° | + | + |
| 5% Fentanyl/95% Methamphetamine | 3°/2° | + | + |
| 10% Fentanyl/90% Methamphetamine | 3°/2° | NT | NT |
| 1% Fentanyl/99% Cocaine | 3°/3° | + | + |
| 5% Fentanyl/95% Cocaine | 3°/3° | + | + |
| 10% Fentanyl/90% Cocaine | 3°/3° | NT | NT |
| 1% Fentanyl/99% Diazepam | 3°/3° | + | − |
| 5% Fentanyl/95% Diazepam | 3°/3° | + | − |
| 10% Fentanyl/90% Diazepam | 3°/3° | NT | NT |

Cobalt Thiocyanate Individual Compound Results

The results for the cobalt thiocyanate testing of the individual compounds are listed in Table 1 above and depicted in FIG. 4. The control displayed a red color. Fentanyl, benzyl fentanyl, NPP, N,N-dimethylaniline, lidocaine, diphenhydramine, levamisole, oxycodone, quinine, methadone, morphine, methamphetamine, cocaine, and methylone all gave a positive response to cobalt thiocyanate, turning blue. Fentanyl and benzyl fentanyl were both very minute but still visible color changes. Furanyl fentanyl, o-fluorofentanyl, lactose, mannitol, boric acid, dopamine, and diazepam were all negative with a color matching that of the control. Some of the compounds were difficult to weigh and as a result excess powder can be seen in FIG. 4.

Eosin Y Mixture Results

The results for the Eosin Y testing containing mixtures of compounds are listed in Table 1 as well as displayed in FIG. 3. Only the 1% mixture results are displayed in FIG. 3. When 1% fentanyl was mixed with any of oxycodone, methadone, morphine, methamphetamine, cocaine, diazepam, boric acid, lactose, mannitol, levamisole, quinine, lidocaine, diphenhydramine, or caffeine, there was a positive response indicated by a pink color change when compared with the control and the cutting agent compound tested individually. All 5% and 10% fentanyl mixture results that were tested also gave positive responses for Eosin Y when compared to the control test strip and the cutting agent when tested individually. Some of the mixtures were difficult to weigh and as a result excess powder can be seen in FIG. 3.

Cobalt Thiocyanate Mixture Results

The results for the cobalt thiocyanate testing of the fentanyl mixtures are listed in Table 1 as well as displayed in FIG. 4. There was a positive color change when compared with the control and the cutting agent tested individually for the following 1% fentanyl mixtures: lidocaine, diphenhydramine, levamisole, oxycodone, methadone, morphine, methamphetamine, and cocaine. There was no observed color change when 1% fentanyl was mixed with the following compounds: lactose, mannitol, caffeine, quinine, boric acid, and diazepam. The results for the 5% and 10% fentanyl mixtures can be found in Table 1. Some of the mixtures were difficult to weigh and as a result excess powder can be seen in FIG. 4.

Determining a Binding Mechanism for Eosin Y

The results for determining a binding mechanism for Eosin Y are listed in Table 1 as well as displayed in FIG. 3. All 3 fentanyl analogues (o-fluorofentanyl, furanylfentanyl, benzylfentanyl) as well as NPP, and N,N-dimethylaniline displayed positive color changes. The color changes exhibited by o-fluorofentanyl, furanylfentanyl and N,N-dimethylaniline were closest to that exhibited by fentanyl. The color changes exhibited by NPP and benzylfentanyl were similar to each other, but not as intense as that of fentanyl, o-fluorofentanyl, furanylfentanyl, and N,N-dimethylaniline. The color change that was observed by NPP and benzylfentanyl was a lighter shade of pink whereas the other fentanyl analogues were brighter shades of pink and more consistent with that observed with fentanyl reacting with Eosin Y.

Discussion

In the present example, it was found that certain compounds elicit the characteristic pink color change when exposed to Eosin Y that indicates a positive response when compared to the control. Not only did hydromorphone and fentanyl react with Eosin Y with a paper assay, but so too did the following compounds: fentanyl, benzylfentanyl, furanylfentanyl, o-fluorofentanyl, NPP, N,N-dimethylaniline, methadone, diphenhydramine, and quinine. From a structural perspective, these compounds all contain a tertiary amine. However, not all tertiary amine-containing compounds tested yielded a positive Eosin Y interaction. Specifically, morphine, oxycodone, cocaine, diazepam, levamisole, lidocaine, and caffeine did not yield a positive Eosin Y interaction. The lack of an Eosin Y interaction with these latter compounds may be the result of steric hindrance based on the nitrogen being placed within the phenanthrene ring or the near proximity of a phenyl substitution. Exposure of the Eosin Y paper to morphine and levamisole did yield a color change but not of the same pink intensity as the other positive responders. The color change observed with morphine and levamisole was more characteristic of orange mixed with pink. While color changes can be subjective, there is a difference in the color that was observed by the positive responders (fentanyl, benzylfentanyl, furanylfentanyl, o-fluorofentanyl, NPP, N,N-dimethylaniline, methadone, diphenhydramine, and quinine) and the other compounds that were tested. Therefore, morphine and levamisole were determined to be negative responders. The other compounds that did not react with Eosin Y either contained no amine group or a primary or secondary amine group.

The testing of 1% fentanyl mixed with 99% of various compounds showed that the Eosin Y paper assay can detect 1% fentanyl. The cobalt thiocyanate paper assay was not consistent in the same manner that the Eosin Y paper assay was in this regard. While the cobalt thiocyanate assay detected 1% fentanyl in some of the mixtures, Eosin Y detected 1% fentanyl in all mixtures. Given that methadone and quinine both gave a false positive in the Eosin Y paper assay, there is difficulty in determining if the color change is due to the presence of fentanyl or from the adulterant drug.

However, all the other drugs that tested negative originally or did not display a positive pink color change when tested without the presence of fentanyl then displayed the positive pink color change once 1% fentanyl was mixed with the drug. This is an indication that Eosin Y can detect fentanyl in low amounts and possibly even lower than 1%. The limits of detection below 1% with the Eosin Y paper assay have not been determined.

The sensitivity of detecting 1% fentanyl is important as only a couple milligrams or less can cause an overdose, and a couple milligrams or less would most likely be the amount found in seized drug samples. Therefore, a test should be sensitive enough to detect low levels of fentanyl. Based on the results, Eosin Y is capable of detecting fentanyl at 1% levels while cobalt thiocyanate by itself is not, thus making it a better choice for a color test to screen for fentanyl in compounds. While fentanyl is not the only compound that will elicit a color change, this test can still assist in narrowing down a drug sample in the early stages of testing and provide an idea of what could potentially be in a drug sample. Although a positive Eosin Y test alone may be supplemented in the field with other tests for enhanced confidence in the detection of the presence of fentanyl, this test can inform an analyst that a harmful substance (fentanyl or an analogue) is possibly present and to proceed with caution. Eosin Y may be used in conjunction with other color tests and instrumentation to identify a drug sample.

In addition, a mechanism by which Eosin Y may be binding to fentanyl was examined. In order to determine a binding mechanism, various fentanyl analogues were chosen and tested based on the substitutions that are present in the structure of these analogues. It is believed that Eosin Y may be binding to either nitrogen in the fentanyl structure. The fentanyl molecule contains a nitrogen in the piperidine ring and a non-piperidine ring nitrogen. The Eosin Y strip contained Eosin Y at a pH of 5 and 7. At these respective pHs, Eosin Y will lose both of the acidic protons and be capable of binding to a nitrogen to form a complex. Furanylfentanyl and o-fluorofentanyl were chosen based on the substitutions present near the tertiary amine of fentanyl, while benzylfentanyl was chosen based on the benzene ring being one carbon closer to the nitrogen within the piperidine ring. When all three compounds were exposed to the Eosin Y test there was a positive pink color change, however o-fluorofentanyl and furanylfentanyl resulted in a more intense pink that was similar to that present with fentanyl alone. The similarity in color changes indicated that the tertiary substituted nitrogen that is not located in the piperidine ring was the primary binding site. In order to further test whether the non-piperidine ring nitrogen is the primary binding site, two compounds (N,N-dimethylaniline and NPP) were tested. These compounds were chosen due to having structures similar to each half of the fentanyl molecule but contained only one nitrogen each as depicted in FIG. 2. The color changes present for each compound would assist in determining which nitrogen was the primary binding site. The structure of NPP resembled the nitrogen in the piperidine ring along with the lower half of the fentanyl molecule, while the structure of N,N-dimethylaniline resembled the tertiary nitrogen not in the piperidine ring along with the upper half of the fentanyl molecule.

Figure 5:
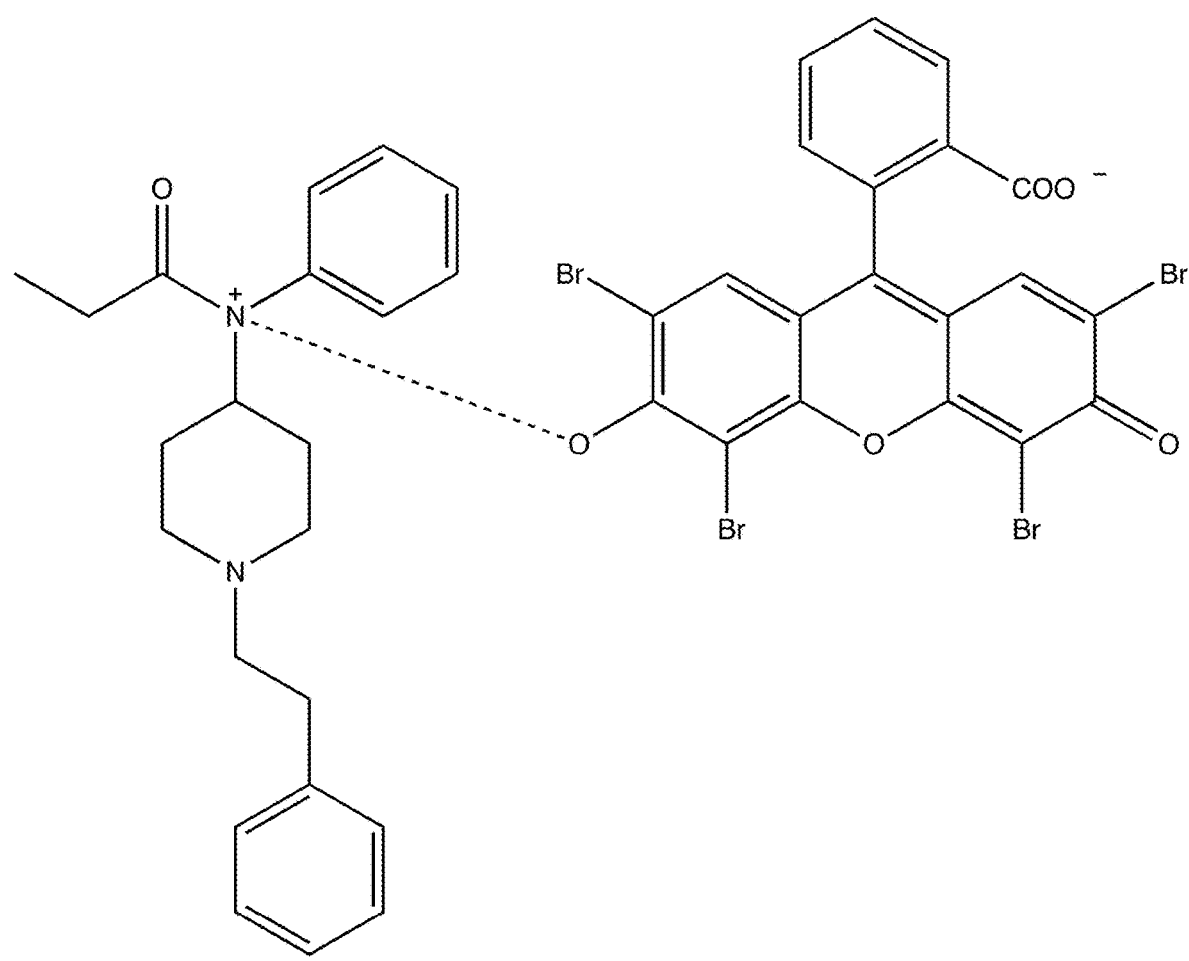
FIG. 5: Mechanism of Eosin Y and primary fentanyl binding site at pH of 5 and 7.

When both compounds were exposed to the Eosin Y test strip, there was a positive pink color observed. Even though both compounds reacted, N,N-dimethylaniline yielded a more intense pink color that resembled the same color change as seen with fentanyl more so than NPP. The similarity of color change between N,N-dimethylaniline and fentanyl indicates that the tertiary nitrogen not located in the piperidine ring is the primary binding site as shown in FIG. 5, but Eosin Y also has the capability of binding to the nitrogen in the piperidine ring as a secondary binding site. It is believed that Eosin Y binding to either nitrogen contributes to the color change seen with fentanyl. Both furanylfentanyl and o-fluorofentanyl yielded similar color changes to fentanyl, even though there were substitutions closer to the non-piperidine ring tertiary amine. These substitutions clearly did not inhibit the binding of Eosin Y which led to similar results as with fentanyl. NPP exhibited a pink color change but it was diminished due to lacking the second nitrogen as a primary binding site. Benzylfentanyl also gave a diminished color change due to the benzene ring being one carbon closer to the piperidine nitrogen. Therefore, this inhibited the secondary binding site and yielded a diminished color change when compared with fentanyl.

Conclusion

Based on the collective current findings from this example, the following conclusions can be drawn about using Eosin Y in a testing assay: (1) Eosin Y is capable of detecting fentanyl in amounts as low as 1% in mixtures of drugs; (2) the color change of Eosin Y is due to binding to select tertiary amines, but not all tertiary amines are capable of binding to Eosin Y; and (3) for fentanyl, the tertiary nitrogen that is not in the piperidine ring of the fentanyl molecule is the primary binding site, while the nitrogen that is in the piperidine ring is a secondary binding site.

Example II—Evaluation of Heroin and Real Crime Scene Samples

A heroin sample was evaluated with an Eosin Y test strip and a cobalt thiocyanate test strip. Furthermore, a sample from a real crime scene, obtained from the Ohio Bureau of Criminal Investigation (BCI), containing fentanyl and caffeine in a mixture, was also evaluated using both an Eosin Y test strip and a cobalt thiocyanate test strip. The results of these tests are shown in FIGS. 6-7.

Figure 6:
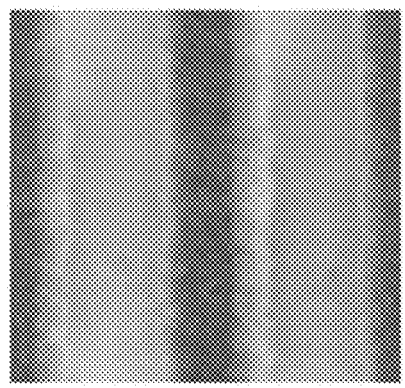
FIG. 6: Results of a screen of heroin samples using Eosin Y (top two images) and cobalt thiocyanate (bottom two images).
Figure 6:
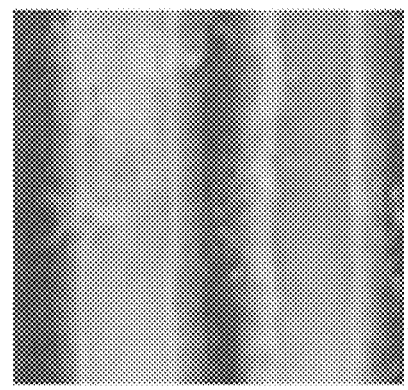
Figure 6:
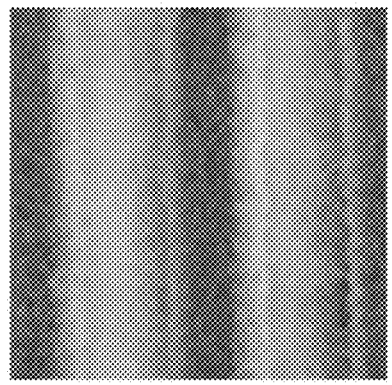
Figure 6:
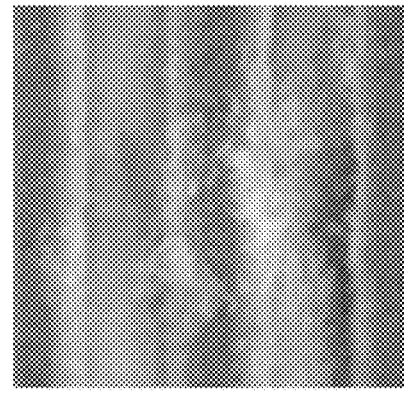

As seen in FIG. 6, the results from the heroin sample are consistent with the results provided in Example I with respect to opioids. In particular, the heroin sample caused color changes similar to the color changes observed with morphine and oxycodone in Example I.

Figure 7A:
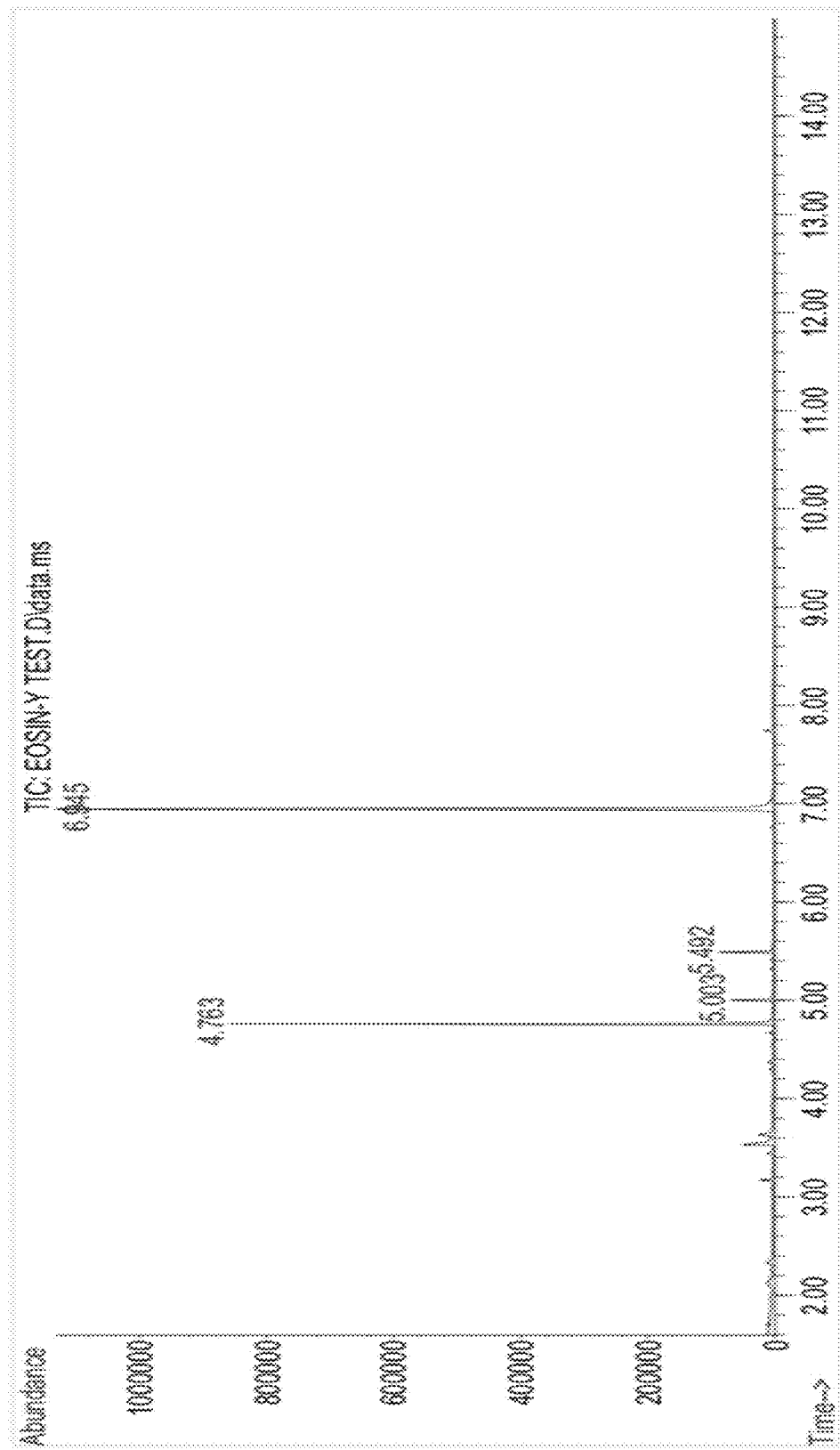
FIGS. 7A-7C: GC/MS results of a crime scene sample containing fentanyl/caffeine in a mixture.
Figure 7B:
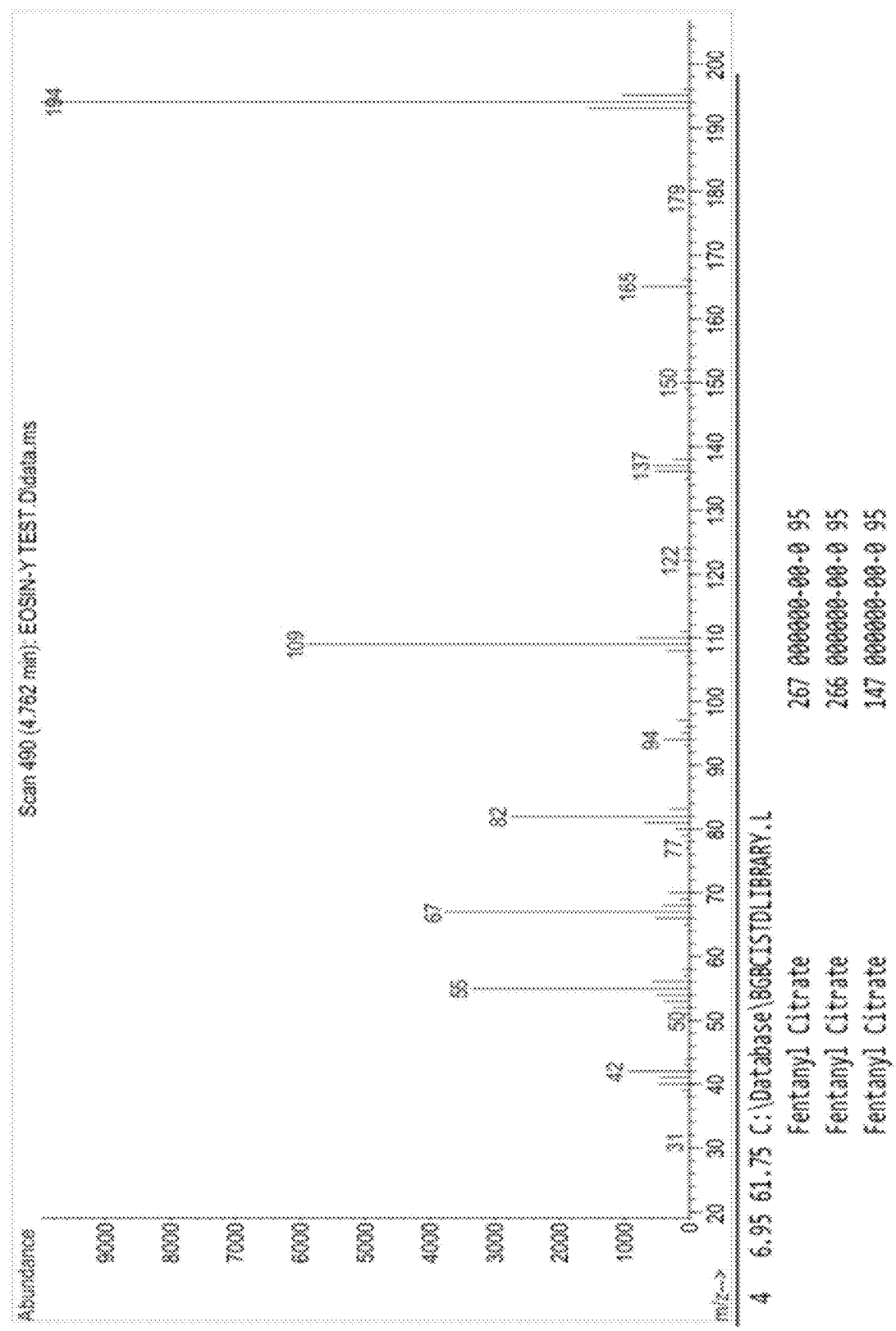
Figure 7C:
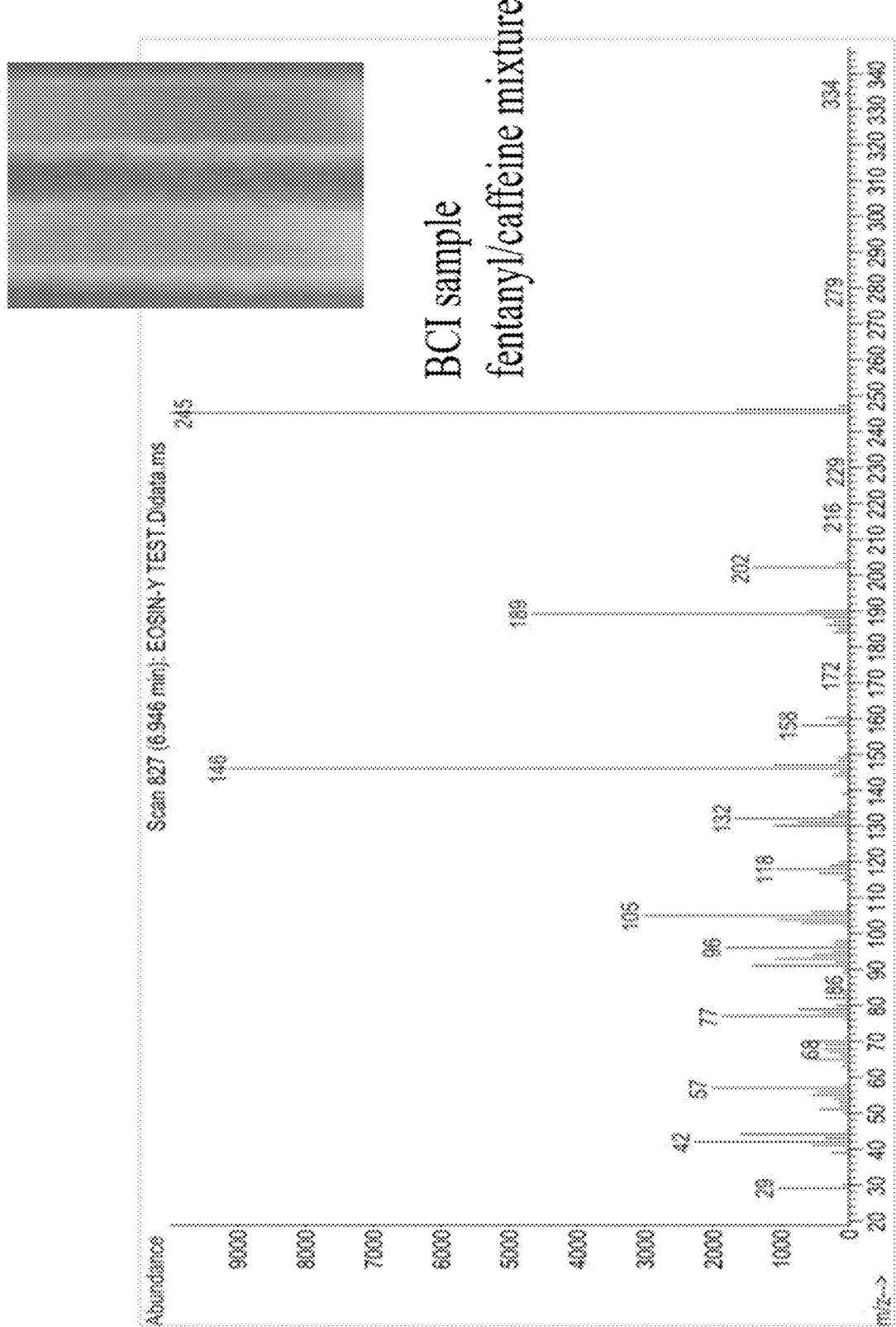

As seen in FIGS. 7A-7C, the BCI sample containing a mixture of fentanyl and caffeine also tested positive, confirming the Eosin Y test in connection with a real-world crime scene sample.

Example III—Evaluation of Cutting Agents and Common Household Powders

To demonstrate that samples can be successfully wicked up by water on a testing card to produce a color change, 12-lane cards were used to analyze a variety of cutting agents and common household powders such as benzocaine, procaine, baking soda, starch, and caffeine, along with various narcotics. Each of the compounds gave a specific bar-code that can be read manually or with a cell phone app. The 12-lane cards had testing reagents coated in each lane designed to test for the following functional groups listed in Table 2. Each compound was swiped across the 12-lane testing card, and bottom edge of the 12-lane testing card was then dipped in water.

TABLE 2

Lane ID and target functional groups of 12-lane testing cards

| Lane | Target functional group(s) |
|---|---|
| A | Quaternary, tertiary, or hindered secondary amines (narcotics, meth, cathinones, and many other pharmaceuticals) |
| B | Quaternary amines, protonated tertiary amines, amines with unusually high pKa values (heroin, crack) |
| C | Quaternary, tertiary, or hindered secondary amines |
| D | Phenols |
| E | Phenols |
| F | Phenols and reducing agents |
| G | Starch (cutting agent) |
| H | Metal chelating groups and reducing agents |
| I | Bases (eg baking soda as cutting agent) |
| J | anilines |
| K | indoles, anilines (cannabinoids, phenethylamines) |
| L | acidic or basic functional groups |

Benzocaine has the following structural formula:

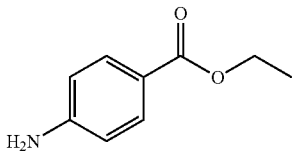

Figure 12:
FIG. 12: Results of tests of benzocaine with a 12-lane testing card.

Benzocaine was tested on the 12-lane testing card. The results are shown in FIG. 12, where it can be seen that a sky blue color in lane A, a yellow/magenta streak in lane J, and a magenta streak in lane K were produced. This shows that benzocaine was successfully wicked up by the water to produce a color change.

Procaine has the following structural formula:

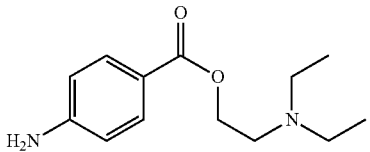 [SMILES: CCN(CC)CCOC(=O)c1ccc(N)cc1]

Figure 13:
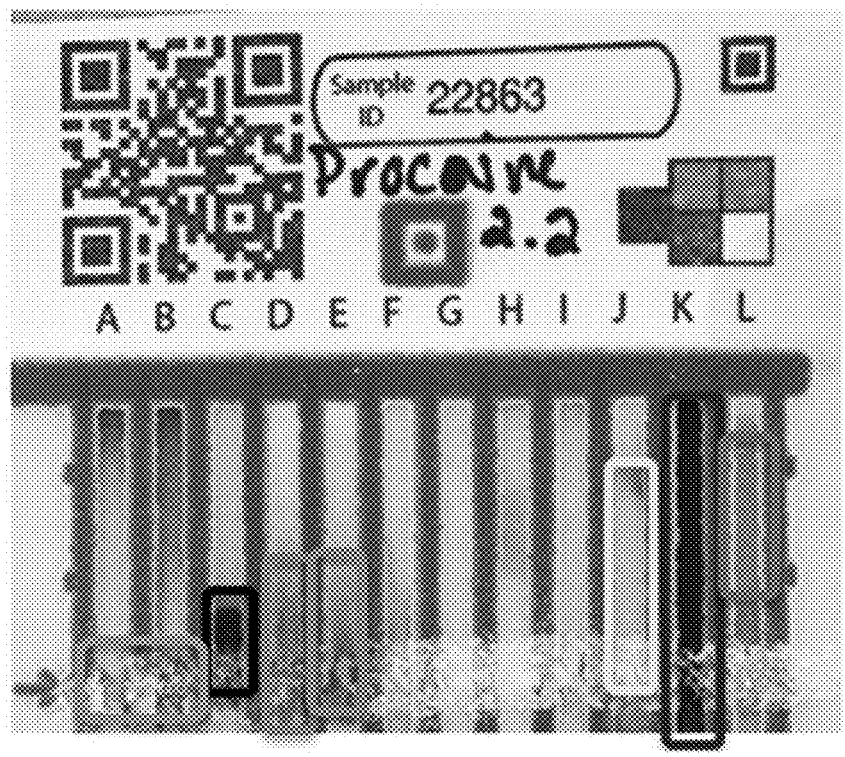
FIG. 13: Results of tests of procaine with a 12-lane testing card.

Procaine was tested on the 12-lane testing card. The results are shown in FIG. 13, where several color changes can be seen. In particular, lane A shows sky blue, lane B shows sky blue, lane C shows black, lane D shows orange, lane E shows orange, lane J shows yellow tipped with red, lane K shows dark purple, and lane L shows blue. This shows that procaine was successfully wicked up by the water to produce color changes.

Figure 14:
FIG. 14: Results of tests of baking soda with a 12-lane testing card.

Baking soda was tested on the 12-lane testing card. The results are shown in FIG. 14, where orange is seen in lane I at the swipe line.

Narcotic samples were tested using the 12-lane testing card. The narcotic samples included heroin, cocaine, crack cocaine, and fentanyl simulant (diethyl carbamazine). In each case, a specific bar code was noticed in Lanes A-D.

Heroin has the following structural formula:

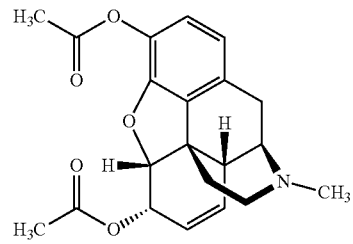

Figure 15:
FIG. 15: Results of tests of heroin with a 12-lane testing card.

Heroin was tested with the 12-lane testing card. The results are shown in FIG. 15. As seen in FIG. 15, lane A showed blue-green, lane B showed blue-green, lane C showed black, and lane D showed a brown streak.

Crack cocaine (free base) has the following structural formula:

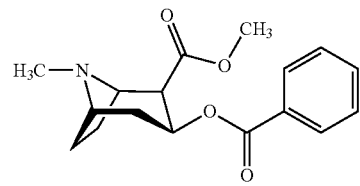

Figure 16:
FIG. 16: Results of tests of crack cocaine with a 12-lane testing card.

Crack cocaine was tested with the 12-lane testing card. The results are shown in FIG. 16. As seen in FIG. 16, lane A showed sky blue at the swipe line, and lane C showed black at the swipe line.

Diethylcarbamazine has the following structural formula:

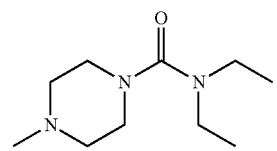

This simulates fentanyl, which has the following structural formula:

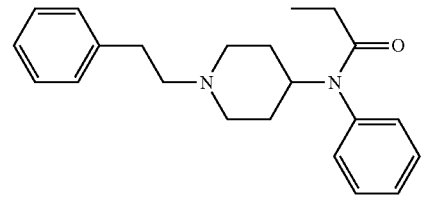 [SMILES: CCC(=O)N(c1ccccc1)C1CCN(CCc2ccccc2)CC1]

Figure 17:
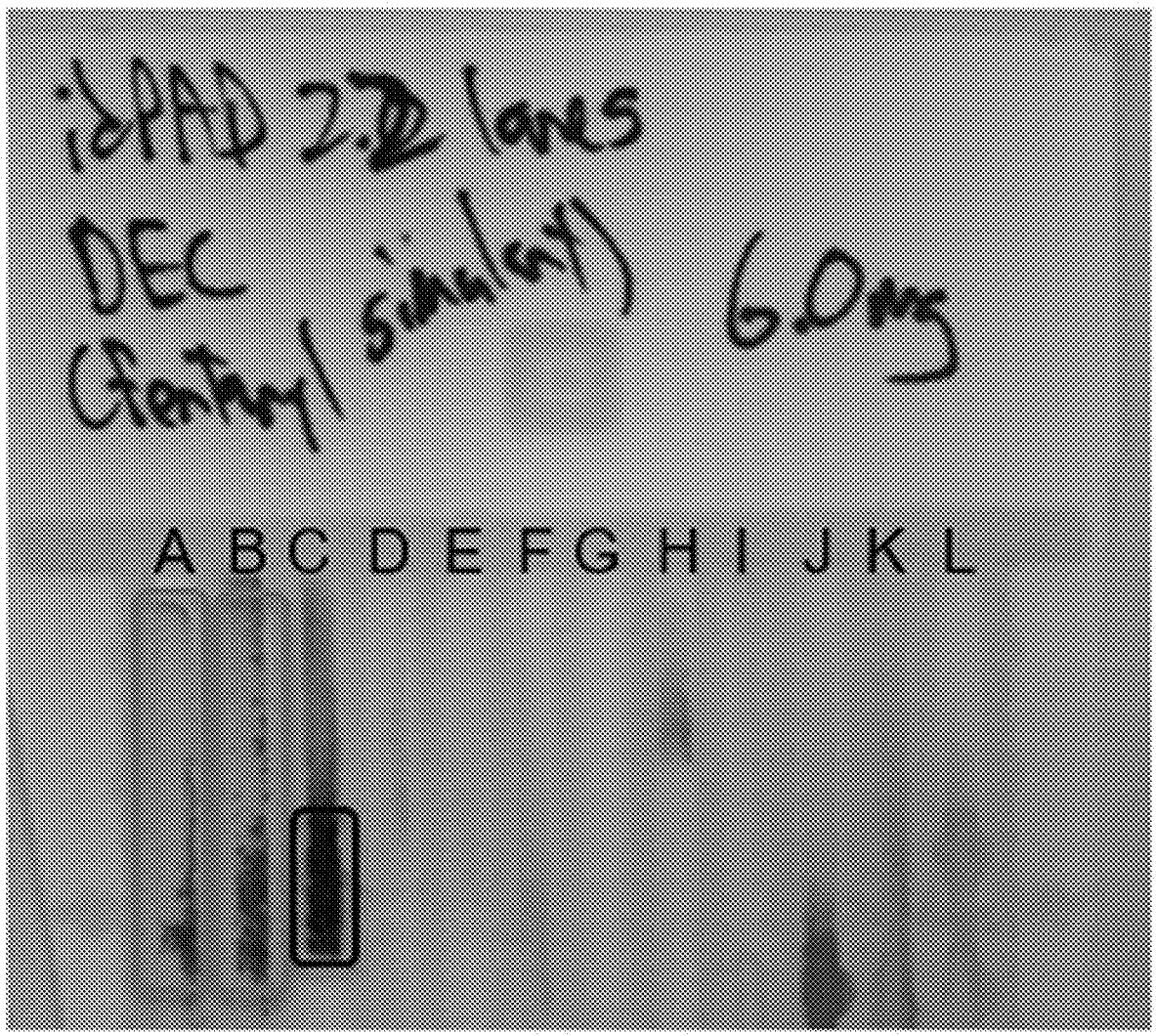
FIG. 17: Results of tests of the fentanyl simulant diethyl carbamazine with a 12-lane testing card.
Figure 18A:
FIGS. 18A-18D: Results of tests with crack cocaine (FIG. 18A), benzocaine (FIG. 18B), a mixture of 33% crack cocaine and 66% benzocaine (FIG. 18C), and a mixture of 11% crack cocaine and 89% benzocaine (FIG. 18D).
Figure 18B:
Figure 18C:
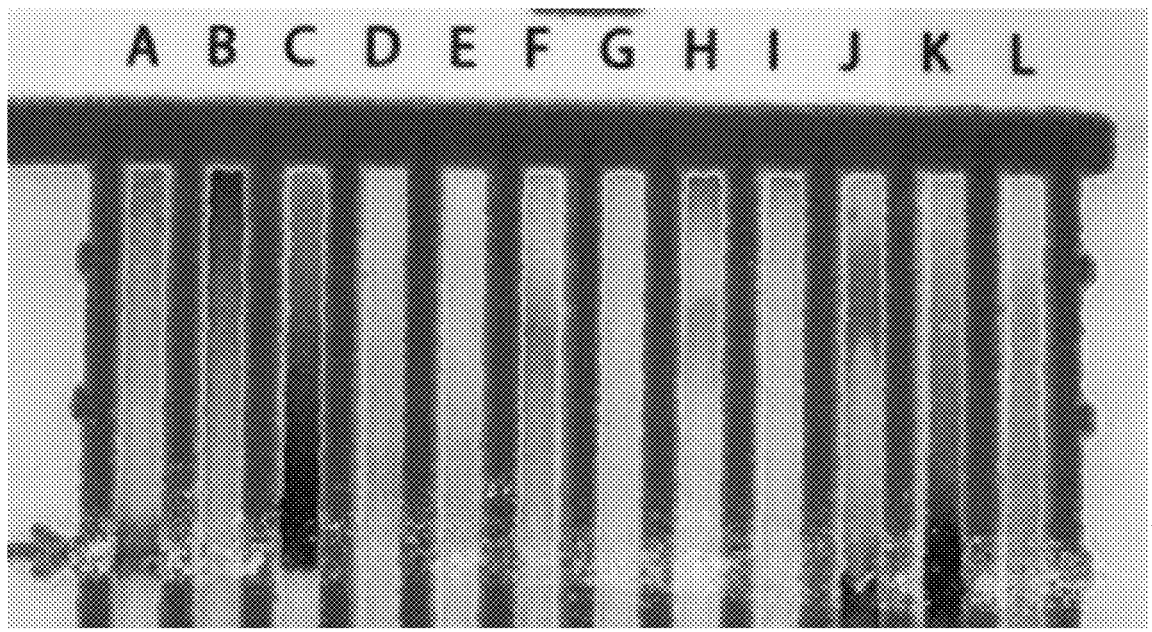
Figure 18D:
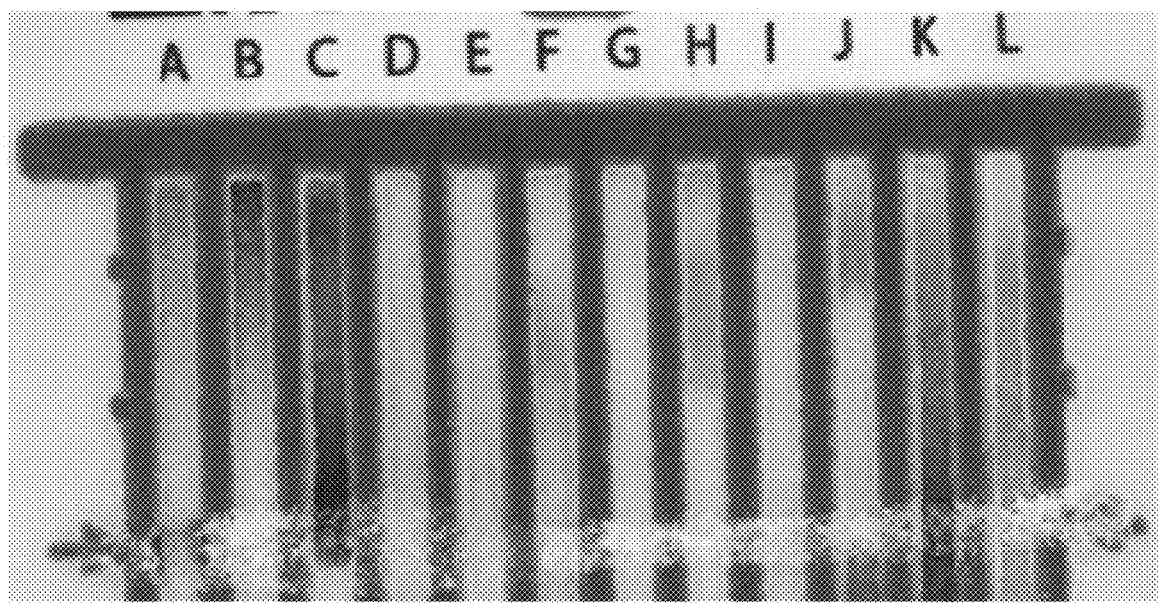

Diethylcarbamazine was tested with the 12-lane testing card. The results are shown in FIG. 17. As seen in FIG. 17, lanes A and B showed blue, and lane C showed black at the swipe line.

Mixtures of crack cocaine and benzocaine at various concentrations were also tested with the 12-lane testing card. FIGS. 18A-18D show the results. As seen from the results, the black color in lane C persisted even at 11% concentration of cocaine in the benzocaine matrix.

Figure 19:
FIG. 19: Results of a test of a street drug sample containing ~1% fentanyl (confirmed by GC).

Street drugs containing fentanyl mixed with heroine and tramadol were also tested with the 12-lane testing card. A street drug sample containing ~1% fentanyl (confirmed by GC) was tested. The results are shown in FIG. 19.

The stability of the test strips was evaluated at various conditions for evaluating stability upon storage. The chemistries were stable after 1 week in loose foil at 4° C. in a refrigerator, at 1 week sealed at room temperature, at 3 months sealed at room temperature, and at 1 week exposed to sun on a window sill.

Mobile Application

A mobile application that can read, analyze, and inform the user of the compound present in an unknown samples was developed. The mobile app consists of two software applications. The first is PAD Calibration which is meant for calibration purposes using PADs run with known compounds. The second is PAD Analysis which is meant for testing whether the color on the lanes from an unknown powder sample correspond to any of the reference standards. FIG. 9 shows snapshots of PAD Calibration and Analysis software using a $25 Android phone.

PAD Calibration: In PAD calibration software, images are loaded for known compounds, analyzed and results stored in a database. The number of known compounds, as well as number of calibration images per compound are configurable. As each image is analyzed, the representative color of a lane and their RGB and HSV values are displayed on the screen. The software can be run with 3-5 compounds and 5-10 calibration images per known compound.

The app was run with images obtained with three compounds chosen to have significant color difference in at least one lane. The first compound was heroin, whereas the other two are obtained using pharmaceutical drugs from a previous version of idPAD. The calibration was performed with 8 images from each compound. The final testing was done with 4 images from each compound. Four negative controls were also tested, in which color of one of the lanes from the 3 compounds above were artificially modified.

Figure 11:
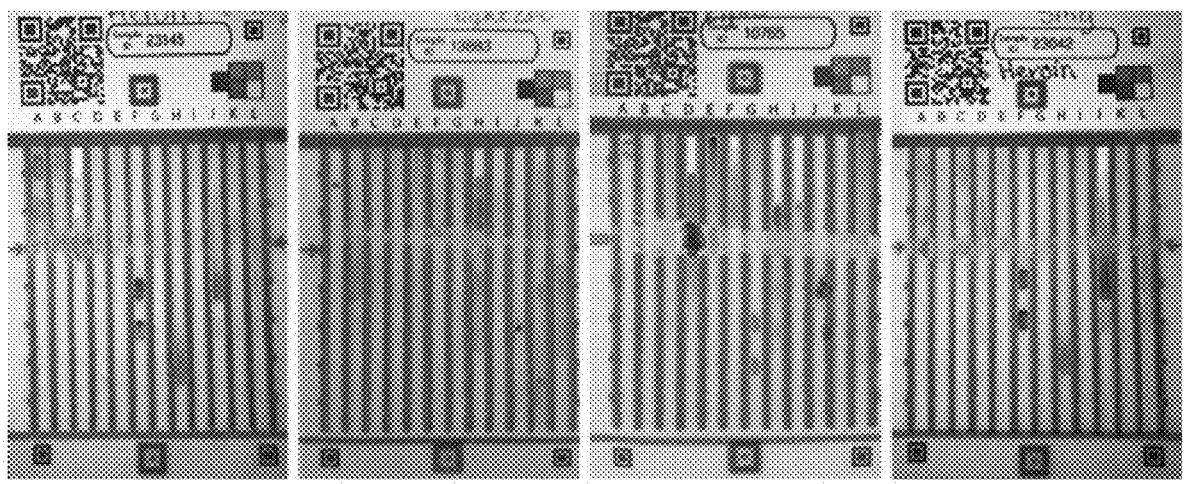
FIG. 11: Representative images of 12-lane testing cards used for calibration and analysis.

FIG. 11 shows representative images used for calibration and analysis. The first three images represent three compounds for calibration. Eight images were used for calibration from each compound, and 4 images were used for testing. The final image represents a negative control age where an artificial color was introduced (light green in lane 2). Four such images were used as negative controls. Out of the 16 images for testing, the compound number was correctly predicted for all of them. For the negative controls, the software correctly predicted that there is no match with any of the three compounds in the database.

Example IV—Eosin Y on a Wipe

Figure 20:
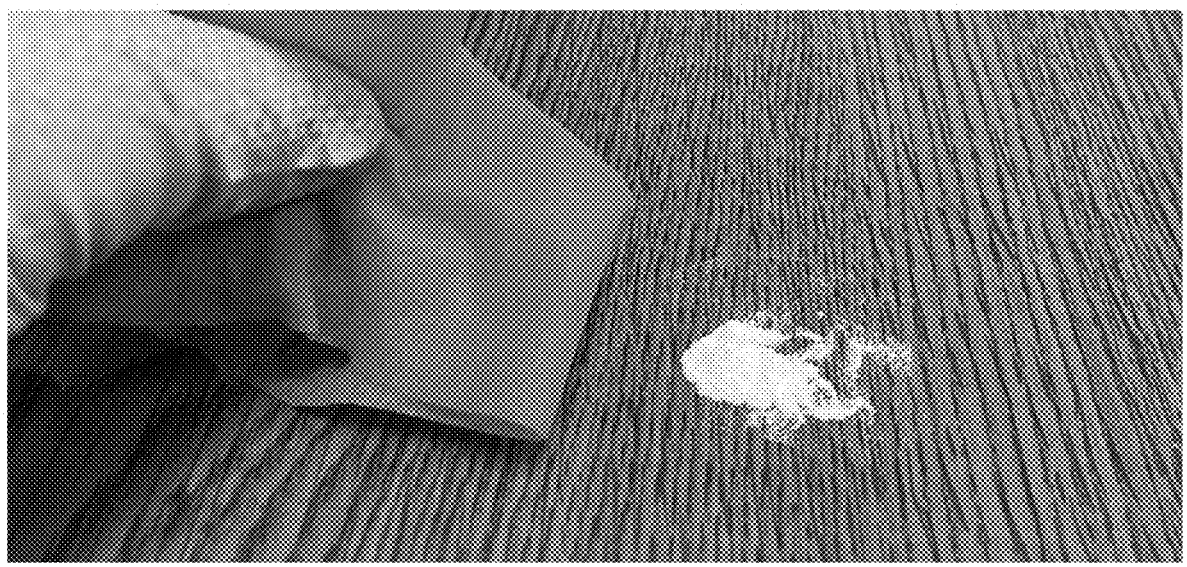
FIG. 20: Photograph showing a wipe saturated with Eosin Y being used to test an unknown powder.
Figure 22A:
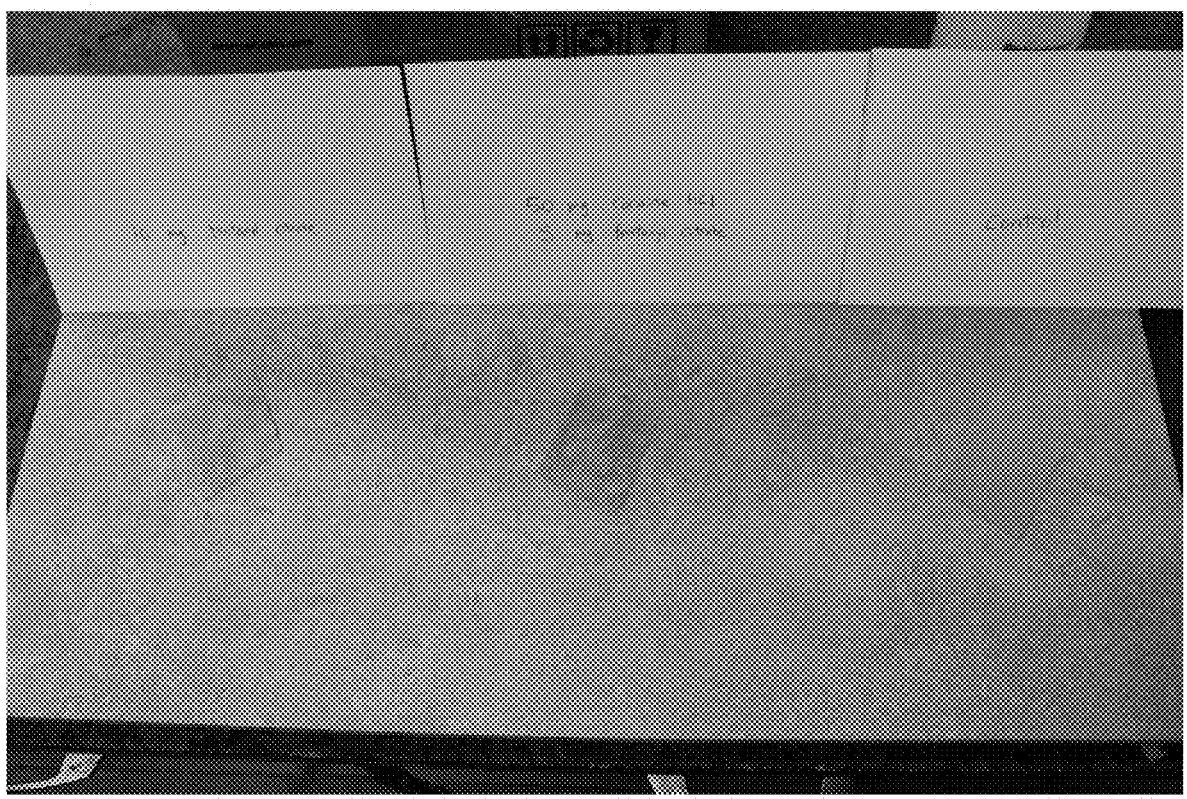
FIGS. 22A-22B: Photographs of wipes with Eosin Y coated thereon after having been contacted with fentanyl (left), a mixture of cocaine and fentanyl (center), or a control without fentanyl (right).
Figure 22B:
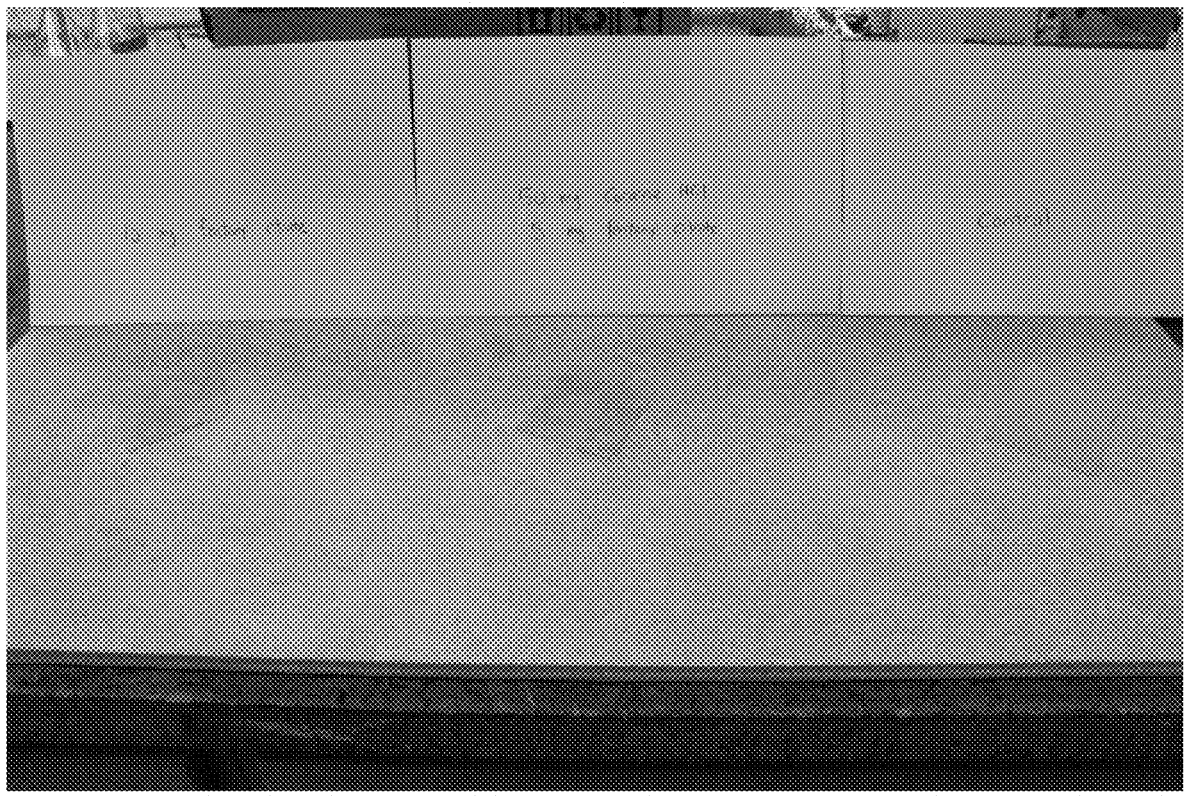

Wipes were saturated with a low concentration Eosin Y solution, and then used to test powders (FIG. 20). The Eosin Y solution included 0.02% Eosin Y, 0.02% phosphotungstic acid, and a citrate buffer. The wipes were tested by contacting them with 10 mg fentanyl citrate, a mixture of 50 mg cocaine HCl and 5 mg fentanyl citrate, or a control without fentanyl which was a bare surface. FIGS. 22A-22B show photographs of the results, from different angles. The pink color change is visible on each of the two wipes that contacted fentanyl, but not on the wipe that was tested with the control.

Certain embodiments of the systems, assays, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the systems, assays, and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A testing assay comprising a substrate having a first area with Eosin Y thereon and a second area having cobalt thiocyanate thereon;
    wherein the first area comprises Eosin Y aggregates created with from 0.005% w/w to 0.2% w/w Eosin Y and from 0.005% w/w to 0.5% w/w phosphotungstic acid in a citrate or phosphate buffer.

2. The testing assay of claim 1, wherein the substrate is a non-woven fabric.

3. The testing assay of claim 1, wherein substrate comprises polyester, polypropylene, nylon, cotton, cotton blends, wood pulp, polyurethane foam, or rayon fibers.

4. The testing assay of claim 1, wherein the substrate is paper.

5. The testing assay of claim 1, wherein the substrate comprises nitrocellulose or cardboard.

6. The testing assay of claim 1, wherein the testing assay is in the form of a wipe having the first area soaked in Eosin Y and the second area soaked in cobalt thiocyanate.

7. The testing assay of claim 1, wherein the first area has Eosin Y at a first pH thereon, and the substrate further comprises a third area having Eosin Y at a second pH thereon.

8. The testing assay of claim 7, wherein the first pH is 5 and the second pH is 7.

9. The testing assay of claim 1, wherein the first area comprises Eosin Y in water at a concentration of 0.02% w/w.

10. The testing assay of claim 1, wherein the first area comprises Eosin Y in water at a concentration ranging from 0.01% w/w to 0.1% w/w.

11. A wipe for testing for opioids, the wipe comprising a fabric substrate comprising Eosin Y in a first area;
    wherein the Eosin Y comprises Eosin Y aggregates created with 0.02% w/w Eosin Y and 0.02% w/w phosphotungstic acid in a citrate or phosphate buffer.

12. A method for detecting the presence of an opioid, the method comprising contacting an unknown substance with the wipe of claim 11, wherein a color change in the first area from orange to pink indicates that the unknown substance is likely, or likely contains, an opioid.

13. A method for detecting the presence of an opioid, the method comprising contacting the testing assay of claim 1 with an unknown substance and immersing the testing assay in water, wherein a color change in the first area from orange to pink and a color change in the second area from orange to blue indicates that the unknown substance is likely, or likely contains, an opioid.

14. A testing assay comprising a substrate having a first area with Eosin Y thereon and a second area having cobalt thiocyanate thereon;
    wherein the first area comprises Eosin Y aggregates created with 0.02% w/w Eosin Y and 0.02% w/w phosphotungstic acid in a citrate or phosphate buffer.

* * * * *